United States Patent
Ding et al.

(10) Patent No.: US 11,179,516 B2
(45) Date of Patent: Nov. 23, 2021

(54) SYSTEMS AND METHODS FOR INCORPORATING PATIENT PRESSURE INTO MEDICAL FLUID DELIVERY

(71) Applicants: BAXTER INTERNATIONAL INC., Deerfield, IL (US); BAXTER HEALTHCARE SA, Glattpark (CH)

(72) Inventors: Yuanpang Ding, Long Grove, IL (US); Ryan Joseph Thomas, Ann Arbor, MI (US); Anders John Wellings, Belleair Beach, FL (US); James Anthony Sloand, Northbrook, IL (US)

(73) Assignees: Baxter International Inc., Deerfield, IL (US); Baxter Healthcare SA, Glattpark (CH)

( * ) Notice: Subject to any disclaimer, the term of this patent is extended or adjusted under 35 U.S.C. 154(b) by 866 days.

(21) Appl. No.: 15/630,536

(22) Filed: Jun. 22, 2017

(65) Prior Publication Data

US 2018/0369477 A1    Dec. 27, 2018

(51) Int. Cl.
*A61M 5/168*    (2006.01)
*A61M 1/14*    (2006.01)
(Continued)

(52) U.S. Cl.
CPC .......... *A61M 5/16831* (2013.01); *A61M 1/14* (2013.01); *A61M 1/28* (2013.01);
(Continued)

(58) Field of Classification Search
CPC ............ A61M 1/14; A61M 2205/3331; A61M 5/16804; A61M 5/16831; A61M 1/28;
(Continued)

(56) References Cited

U.S. PATENT DOCUMENTS

| | | |
|---|---|---|
| 2,286,613 A | 1/1942 | Fuller |
| 2,705,223 A | 3/1955 | Renfrew et al. |

(Continued)

FOREIGN PATENT DOCUMENTS

| | | |
|---|---|---|
| DE | 1226740 | 10/1966 |
| DE | 3522782 A1 | 1/1987 |

(Continued)

*Primary Examiner* — Brandy S Lee
(74) *Attorney, Agent, or Firm* — K&L Gates LLP

(57) ABSTRACT

A medical fluid delivery machine includes a pump interface having an actuation area for delivering positive or negative pressure to a medical fluid handling device; a pressure sensor positioned to measure pressure within the actuation area; a valve positioned to selectively vent the actuation area to atmosphere; and a control unit in signal communication with the pressure sensor and control communication with the valve, the control unit performing a sequence during pumping, wherein (i) application of positive pressure or negative pressure to the actuation area is stopped, the valve is switched to vent the actuation area to atmosphere, then switched to close the actuation area to atmosphere, and at least one pressure signal reading is taken via the pressure sensor, and (ii) a determination is made whether positive pressure or negative pressure to the chamber should be resumed based on the at least one pressure signal reading.

21 Claims, 5 Drawing Sheets

(51) Int. Cl.
*G05D 7/06* (2006.01)
*A61M 1/28* (2006.01)

(52) U.S. Cl.
CPC ............ *A61M 5/16804* (2013.01); *G05D 7/06* (2013.01); *A61M 2205/12* (2013.01); *A61M 2205/3331* (2013.01); *A61M 2205/3344* (2013.01)

(58) Field of Classification Search
CPC ...... A61M 2205/12; A61M 2205/3344; G05D 7/06
See application file for complete search history.

(56) References Cited

U.S. PATENT DOCUMENTS

| | | |
|---|---|---|
| 2,971,876 A | 2/1961 | Phair |
| 3,255,923 A | 6/1966 | Soto |
| 3,327,115 A | 6/1967 | Barlett |
| 3,375,300 A | 3/1968 | Ropp |
| 3,428,828 A | 2/1969 | Korzekwa et al. |
| 3,485,245 A | 12/1969 | Lahr et al. |
| 3,494,897 A | 2/1970 | Reding et al. |
| 3,507,708 A | 4/1970 | Vingnaud |
| 3,514,359 A | 5/1970 | Frese |
| 3,561,493 A | 2/1971 | Maillard |
| 3,620,215 A | 11/1971 | Tysk et al. |
| 3,626,670 A | 12/1971 | Pecker |
| 3,645,992 A | 2/1972 | Elston |
| 3,656,873 A | 4/1972 | Schiff |
| 3,689,204 A | 9/1972 | Prisk |
| 3,703,959 A | 11/1972 | Raymond |
| 3,707,967 A | 1/1973 | Kitrilakis et al. |
| 3,709,222 A | 1/1973 | Devries |
| 3,772,136 A | 11/1973 | Workman |
| 3,792,643 A | 2/1974 | Scheafer |
| 3,814,799 A | 6/1974 | Wygasch |
| 3,816,033 A | 6/1974 | Fried et al. |
| 3,858,581 A | 1/1975 | Kamen |
| 3,902,490 A | 9/1975 | Jacobsen |
| 3,912,843 A | 10/1975 | Brazier |
| 3,937,758 A | 2/1976 | Castagna |
| 3,955,901 A | 5/1976 | Hamilton |
| 3,966,358 A | 6/1976 | Heimes et al. |
| 3,976,574 A | 8/1976 | White |
| 3,979,284 A | 9/1976 | Granger |
| 3,995,084 A | 11/1976 | Berger et al. |
| 4,041,103 A | 8/1977 | Davison et al. |
| 4,058,647 A | 11/1977 | Inoue et al. |
| 4,071,040 A | 1/1978 | Moriarty |
| 4,086,653 A | 4/1978 | Gernes |
| 4,087,587 A | 5/1978 | Shida et al. |
| 4,087,588 A | 5/1978 | Shida et al. |
| 4,095,012 A | 6/1978 | Schirmer |
| 4,096,859 A | 6/1978 | Agarwal et al. |
| 4,110,303 A | 8/1978 | Gergen et al. |
| 4,122,947 A | 10/1978 | Falla |
| 4,126,132 A | 11/1978 | Portner et al. |
| 4,137,915 A | 2/1979 | Kamen |
| 4,140,118 A | 2/1979 | Jassawalla |
| 4,142,524 A | 3/1979 | Jassawalla et al. |
| 4,147,827 A | 4/1979 | Breidt, Jr. et al. |
| 4,158,530 A | 6/1979 | Bernstein |
| 4,181,245 A | 1/1980 | Garrett et al. |
| 4,184,497 A | 1/1980 | Kolff et al. |
| 4,187,057 A | 2/1980 | Xanthopoulos |
| 4,199,307 A | 4/1980 | Jassawalla |
| 4,211,519 A | 7/1980 | Hogan |
| 4,233,367 A | 11/1980 | Ticknor et al. |
| 4,235,231 A | 11/1980 | Schindler et al. |
| 4,236,880 A | 12/1980 | Archibald |
| 4,239,041 A | 12/1980 | Popovich et al. |
| 4,240,408 A | 12/1980 | Schael |
| 4,243,619 A | 1/1981 | Fraser et al. |
| 4,252,651 A | 2/1981 | Soderstrom |
| 4,265,601 A | 5/1981 | Mandroian |
| 4,273,121 A | 6/1981 | Jassawalla |
| 4,277,226 A | 7/1981 | Archibald |
| 4,286,597 A | 9/1981 | Gajewski |
| 4,298,714 A | 11/1981 | Levin et al. |
| 4,303,376 A | 12/1981 | Siekmann |
| 4,306,976 A | 12/1981 | Bazzato |
| 4,310,141 A | 1/1982 | Tamura |
| 4,316,466 A | 2/1982 | Babb |
| 4,322,465 A | 3/1982 | Webster |
| 4,322,480 A | 3/1982 | Tuller et al. |
| D264,134 S | 4/1982 | Xanthopoulos |
| 4,327,726 A | 5/1982 | Kwong et al. |
| 4,332,655 A | 6/1982 | Berejka |
| 4,333,088 A | 6/1982 | Diggins |
| 4,334,838 A | 6/1982 | Fessler et al. |
| 4,336,352 A | 6/1982 | Sakurai et al. |
| 4,338,190 A | 7/1982 | Kraus et al. |
| 4,351,333 A | 9/1982 | Lazarus et al. |
| 4,368,737 A | 1/1983 | Ash |
| 4,375,346 A | 3/1983 | Kraus et al. |
| 4,381,003 A | 4/1983 | Buoncristiani |
| 4,381,005 A | 4/1983 | Bujan |
| 4,382,753 A | 5/1983 | Archibald |
| 4,387,184 A | 6/1983 | Coquard et al. |
| 4,391,600 A | 7/1983 | Archibald |
| 4,396,382 A | 8/1983 | Goldhaber |
| 4,398,910 A | 8/1983 | Blake et al. |
| 4,402,694 A | 9/1983 | Ash et al. |
| 4,405,667 A | 9/1983 | Chirstensen et al. |
| 4,405,774 A | 9/1983 | Miwa et al. |
| 4,407,877 A | 10/1983 | Rasmussen |
| 4,407,888 A | 10/1983 | Crofts |
| 4,410,164 A | 10/1983 | Kamen |
| 4,410,322 A | 10/1983 | Archibald |
| 4,411,649 A | 10/1983 | Kamen |
| 4,412,917 A | 11/1983 | Ahjopalo |
| 4,417,753 A | 11/1983 | Bacehowski |
| 4,429,076 A | 1/1984 | Saito et al. |
| D272,651 S | 2/1984 | Mahurkar |
| 4,430,048 A | 2/1984 | Fritsch |
| 4,438,238 A | 3/1984 | Fukushima et al. |
| 4,449,976 A | 5/1984 | Kamen |
| 4,456,218 A | 6/1984 | Kawabata et al. |
| 4,464,172 A | 8/1984 | Lichtenstein |
| 4,465,481 A | 8/1984 | Blake |
| 4,468,222 A | 8/1984 | Lundquist |
| 4,472,116 A | 9/1984 | Wenstrup |
| 4,472,117 A | 9/1984 | Wenstrup |
| 4,473,342 A | 9/1984 | Iles |
| 4,479,760 A | 10/1984 | Bilstad et al. |
| 4,479,761 A | 10/1984 | Bilstad et al. |
| 4,479,762 A | 10/1984 | Bilstad et al. |
| 4,479,989 A | 10/1984 | Mahal |
| 4,482,584 A | 11/1984 | Hess et al. |
| 4,490,137 A | 12/1984 | Moukheibir |
| 4,496,349 A | 1/1985 | Cosentino |
| 4,498,902 A | 2/1985 | Ash et al. |
| 4,504,038 A | 3/1985 | King |
| 4,521,437 A | 6/1985 | Storms |
| 4,530,759 A | 7/1985 | Schal |
| 4,537,561 A | 8/1985 | Xanthopoulos |
| 4,543,087 A | 9/1985 | Sommercorn et al. |
| 4,547,136 A | 10/1985 | Rothstein |
| 4,548,348 A | 10/1985 | Clements |
| 4,552,552 A | 11/1985 | Polaschegg et al. |
| 4,559,036 A | 12/1985 | Wunsch |
| 4,559,044 A | 12/1985 | Robinson et al. |
| 4,560,472 A | 12/1985 | Granzow et al. |
| 4,562,118 A | 12/1985 | Maruhashi et al. |
| 4,568,723 A | 2/1986 | Lu |
| 4,573,994 A | 3/1986 | Fischell et al. |
| 4,574,173 A | 3/1986 | Bennett |
| 4,581,012 A | 4/1986 | Brown et al. |
| 4,585,436 A | 4/1986 | Davis et al. |
| 4,586,920 A | 5/1986 | Peabody |
| 4,588,648 A | 5/1986 | Krueger |
| 4,599,055 A | 7/1986 | Dykstra |
| 4,599,276 A | 7/1986 | Martini |

(56) References Cited

U.S. PATENT DOCUMENTS

| | | |
|---|---|---|
| 4,600,401 A | 7/1986 | Kamen |
| 4,613,327 A | 9/1986 | Tegrarian et al. |
| 4,614,778 A | 9/1986 | Kajiura et al. |
| 4,618,343 A | 10/1986 | Polaschegg |
| 4,620,690 A | 11/1986 | Kamen |
| RE32,303 E | 12/1986 | Lasker et al. |
| 4,627,844 A | 12/1986 | Schmitt |
| 4,628,969 A | 12/1986 | Jurgens, Jr. et al. |
| 4,634,426 A | 1/1987 | Kamen |
| 4,634,430 A | 1/1987 | Polaschegg |
| 4,636,412 A | 1/1987 | Field |
| 4,639,245 A | 1/1987 | Pastrone et al. |
| 4,640,870 A | 2/1987 | Akazawa et al. |
| 4,642,098 A | 2/1987 | Lundquist |
| 4,643,926 A | 2/1987 | Mueller |
| 4,648,810 A | 3/1987 | Schippers et al. |
| 4,648,872 A | 3/1987 | Kamen |
| 4,657,490 A | 4/1987 | Abbott |
| 4,660,568 A | 4/1987 | Cosman |
| 4,668,752 A | 5/1987 | Tominari et al. |
| 4,673,334 A | 6/1987 | Allington et al. |
| 4,681,564 A | 7/1987 | Landreneau |
| 4,681,797 A | 7/1987 | Van Iseghem |
| 4,686,125 A | 8/1987 | Johnston et al. |
| 4,687,471 A | 8/1987 | Twardowski et al. |
| 4,692,361 A | 9/1987 | Johnston et al. |
| 4,694,848 A | 9/1987 | Jorgensen et al. |
| 4,696,671 A | 9/1987 | Epstein et al. |
| 4,703,773 A | 11/1987 | Hansen et al. |
| 4,704,102 A | 11/1987 | Guthery |
| 4,707,389 A | 11/1987 | Ward |
| 4,710,166 A | 12/1987 | Thompson et al. |
| 4,717,117 A | 1/1988 | Cook |
| 4,718,890 A | 1/1988 | Peabody |
| 4,724,028 A | 2/1988 | Zabielski et al. |
| 4,726,997 A | 2/1988 | Mueller et al. |
| 4,732,795 A | 3/1988 | Ohya et al. |
| 4,734,327 A | 3/1988 | Vicik |
| 4,735,558 A | 4/1988 | Kienholz et al. |
| 4,735,855 A | 4/1988 | Wofford et al. |
| 4,740,582 A | 4/1988 | Coquard et al. |
| 4,747,822 A | 5/1988 | Peabody |
| 4,749,109 A | 6/1988 | Kamen |
| 4,753,222 A | 6/1988 | Morishita |
| 4,760,114 A | 7/1988 | Haaf et al. |
| 4,762,864 A | 8/1988 | Goel et al. |
| 4,764,404 A | 8/1988 | Genske et al. |
| 4,767,377 A | 8/1988 | Falla |
| 4,767,651 A | 8/1988 | Starczweski et al. |
| 4,769,134 A | 9/1988 | Allan et al. |
| 4,772,269 A | 9/1988 | Twardowski et al. |
| 4,772,497 A | 9/1988 | Maasola |
| 4,778,356 A | 10/1988 | Hicks |
| 4,778,450 A | 10/1988 | Kamen |
| 4,778,451 A | 10/1988 | Kamen |
| 4,778,697 A | 10/1988 | Genske et al. |
| 4,784,576 A | 11/1988 | Bloom et al. |
| 4,786,697 A | 11/1988 | Cozewith et al. |
| 4,789,714 A | 12/1988 | Cozewith et al. |
| 4,792,488 A | 12/1988 | Schirmer |
| 4,794,942 A | 1/1989 | Yasuda et al. |
| 4,795,782 A | 1/1989 | Lutz et al. |
| 4,798,580 A | 1/1989 | DeMeo et al. |
| 4,800,129 A | 1/1989 | Deak |
| 4,803,102 A | 2/1989 | Raniere et al. |
| 4,808,161 A | 2/1989 | Kamen |
| 4,816,019 A | 3/1989 | Kamen |
| 4,816,343 A | 3/1989 | Mueller |
| 4,818,186 A | 4/1989 | Pastrone et al. |
| 4,818,190 A | 4/1989 | Pelmulder et al. |
| 4,823,552 A | 4/1989 | Ezell et al. |
| 4,824,339 A | 4/1989 | Bainbridge et al. |
| 4,826,482 A | 5/1989 | Kamen |
| 4,828,545 A | 5/1989 | Epstein et al. |
| 4,830,586 A | 5/1989 | Herter et al. |
| 4,832,054 A | 5/1989 | Bark |
| 4,834,755 A | 5/1989 | Silvestrini et al. |
| 4,842,582 A | 6/1989 | Mahurkar |
| 4,842,584 A | 6/1989 | Pastrone |
| 4,842,948 A | 6/1989 | Gagliani et al. |
| 4,848,722 A | 7/1989 | Webster |
| 4,850,805 A | 7/1989 | Madsen et al. |
| 4,852,851 A | 8/1989 | Webster |
| 4,855,356 A | 8/1989 | Holub et al. |
| 4,856,259 A | 8/1989 | Woo et al. |
| 4,856,260 A | 8/1989 | Woo et al. |
| 4,859,319 A | 8/1989 | Borsari |
| 4,861,242 A | 8/1989 | Finsterwald |
| 4,863,996 A | 9/1989 | Nakazima et al. |
| 4,865,584 A | 9/1989 | Epstein et al. |
| 4,871,799 A | 10/1989 | Kobayashi et al. |
| 4,872,813 A | 10/1989 | Gorton et al. |
| 4,873,287 A | 10/1989 | Holub et al. |
| 4,874,808 A | 10/1989 | Syuji et al. |
| 4,877,682 A | 10/1989 | Sauers et al. |
| 4,885,119 A | 12/1989 | Mueller et al. |
| 4,886,431 A | 12/1989 | Soderquist et al. |
| 4,886,432 A | 12/1989 | Kimberlin |
| 4,895,561 A | 1/1990 | Mahurkar |
| 4,904,168 A | 2/1990 | Cavoto et al. |
| 4,910,085 A | 3/1990 | Raniere et al. |
| 4,923,470 A | 5/1990 | Dumican |
| 4,927,411 A | 5/1990 | Pastrone et al. |
| 4,929,479 A | 5/1990 | Shishido et al. |
| 4,931,520 A | 6/1990 | Yamanashi et al. |
| 4,935,004 A | 6/1990 | Cruz |
| 4,937,299 A | 6/1990 | Ewen et al. |
| 4,941,519 A | 7/1990 | Sestak et al. |
| 4,942,735 A | 7/1990 | Mushika et al. |
| 4,946,616 A | 8/1990 | Falla et al. |
| 4,950,720 A | 8/1990 | Randall, Jr. et al. |
| 4,957,966 A | 9/1990 | Nishio et al. |
| 4,957,967 A | 9/1990 | Mizuno et al. |
| 4,966,795 A | 10/1990 | Genske et al. |
| 4,976,162 A | 12/1990 | Kamen |
| 4,977,213 A | 12/1990 | Giroud-Abel et al. |
| 4,990,054 A | 2/1991 | Janocko |
| 4,992,511 A | 2/1991 | Yamamoto et al. |
| 4,996,054 A | 2/1991 | Pietsch et al. |
| 4,999,254 A | 3/1991 | Ofstein |
| 5,002,471 A | 3/1991 | Perlov |
| 5,003,019 A | 3/1991 | Ishimaru et al. |
| 5,004,459 A | 4/1991 | Peabody et al. |
| 5,006,050 A | 4/1991 | Cooke et al. |
| 5,006,601 A | 4/1991 | Lutz et al. |
| 5,008,204 A | 4/1991 | Stehling |
| 5,008,356 A | 4/1991 | Ishimaru et al. |
| 5,017,652 A | 5/1991 | Abe et al. |
| 5,019,140 A | 5/1991 | Bowser et al. |
| 5,034,457 A | 7/1991 | Serini et al. |
| 5,034,458 A | 7/1991 | Serini et al. |
| 5,037,385 A | 8/1991 | O'Byrne |
| 5,043,088 A | 8/1991 | Falla |
| 5,044,902 A | 9/1991 | Malbec |
| 5,053,023 A | 10/1991 | Martin |
| 5,053,457 A | 10/1991 | Lee |
| 5,057,073 A | 10/1991 | Martin |
| 5,057,075 A | 10/1991 | Moncrief et al. |
| 5,062,774 A | 11/1991 | Kramer et al. |
| 5,071,686 A | 12/1991 | Genske et al. |
| 5,071,911 A | 12/1991 | Furuta et al. |
| 5,071,912 A | 12/1991 | Furuta et al. |
| 5,075,376 A | 12/1991 | Furuta et al. |
| 5,079,295 A | 1/1992 | Furuta et al. |
| 5,085,649 A | 2/1992 | Flynn |
| 5,087,677 A | 2/1992 | Brekner et al. |
| 5,088,515 A | 2/1992 | Kamen |
| 5,093,164 A | 3/1992 | Bauer et al. |
| 5,093,194 A | 3/1992 | Touhsaent et al. |
| 5,094,820 A | 3/1992 | Maxwell et al. |
| 5,094,921 A | 3/1992 | Itamura et al. |
| 5,098,262 A | 3/1992 | Wecker et al. |
| 5,098,413 A | 3/1992 | Trudell et al. |
| 5,106,366 A | 4/1992 | Steppe |

(56) References Cited

U.S. PATENT DOCUMENTS

| | | |
|---|---|---|
| 5,106,368 A | 4/1992 | Uldall et al. |
| 5,106,920 A | 4/1992 | Murakami et al. |
| 5,108,844 A | 4/1992 | Blumberg et al. |
| 5,110,642 A | 5/1992 | Genske et al. |
| 5,116,906 A | 5/1992 | Mizuno et al. |
| 5,120,303 A | 6/1992 | Hombrouckx |
| 5,125,891 A | 6/1992 | Hossain et al. |
| 5,129,894 A | 7/1992 | Sommermeyer et al. |
| 5,132,363 A | 7/1992 | Furuta et al. |
| 5,133,650 A | 7/1992 | Sunderland et al. |
| 5,135,485 A | 8/1992 | Cohen et al. |
| 5,135,785 A | 8/1992 | Milton |
| 5,141,493 A | 8/1992 | Jacobsen et al. |
| 5,145,731 A | 9/1992 | Lund et al. |
| 5,154,979 A | 10/1992 | Kerschbaumer et al. |
| 5,159,004 A | 10/1992 | Furuta et al. |
| 5,163,900 A | 11/1992 | Wortrich |
| 5,164,267 A | 11/1992 | D'Heur et al. |
| 5,176,634 A | 1/1993 | Smith et al. |
| 5,176,956 A | 1/1993 | Jevne et al. |
| 5,178,182 A | 1/1993 | Kamen |
| 5,183,706 A | 2/1993 | Bekele |
| 5,185,084 A | 2/1993 | Lapidus et al. |
| 5,185,189 A | 2/1993 | Stenger et al. |
| 5,188,593 A | 2/1993 | Martin |
| 5,189,091 A | 2/1993 | Laughner |
| 5,193,913 A | 3/1993 | Rosenbaum |
| 5,193,990 A | 3/1993 | Kamen et al. |
| 5,194,316 A | 3/1993 | Horner et al. |
| 5,195,960 A | 3/1993 | Hossain et al. |
| 5,195,986 A | 3/1993 | Kamen |
| 5,196,254 A | 3/1993 | Alliyama |
| 5,197,951 A | 3/1993 | Mahurkar |
| 5,203,943 A | 4/1993 | Nornberg et al. |
| 5,206,290 A | 4/1993 | Mizuno et al. |
| 5,207,642 A | 5/1993 | Orkin et al. |
| 5,207,650 A | 5/1993 | Martin |
| 5,207,983 A | 5/1993 | Liebert et al. |
| 5,209,723 A | 5/1993 | Twardowski et al. |
| 5,211,201 A | 5/1993 | Kamen et al. |
| 5,212,238 A | 5/1993 | Schelbelhoffer et al. |
| 5,213,483 A | 5/1993 | Flaherty et al. |
| 5,215,312 A | 6/1993 | Knappe et al. |
| 5,215,450 A | 6/1993 | Tamari |
| 5,218,048 A | 6/1993 | Abe et al. |
| 5,218,049 A | 6/1993 | Yamamoto et al. |
| 5,221,255 A | 6/1993 | Mahurkar et al. |
| 5,221,256 A | 6/1993 | Mahurkar |
| 5,222,946 A | 6/1993 | Kamen |
| 5,230,614 A | 7/1993 | Zanger et al. |
| 5,230,934 A | 7/1993 | Sakano et al. |
| 5,230,935 A | 7/1993 | Delimoy et al. |
| 5,238,997 A | 8/1993 | Bauer et al. |
| 5,241,985 A | 9/1993 | Faust et al. |
| 5,244,971 A | 9/1993 | Jean-Marc |
| 5,245,151 A | 9/1993 | Chamberlain et al. |
| 5,245,693 A | 9/1993 | Ford et al. |
| 5,247,434 A | 9/1993 | Peterson et al. |
| 5,250,027 A | 10/1993 | Lewis et al. |
| 5,250,041 A | 10/1993 | Folden et al. |
| 5,252,044 A | 10/1993 | Raines et al. |
| 5,254,084 A | 10/1993 | Geary |
| 5,254,824 A | 10/1993 | Chamberlain et al. |
| 5,257,917 A | 11/1993 | Minarik et al. |
| 5,258,230 A | 11/1993 | La Fleur et al. |
| 5,272,235 A | 12/1993 | Wakatsuru et al. |
| 5,277,820 A | 1/1994 | Ash |
| 5,278,231 A | 1/1994 | Chundury |
| 5,278,377 A | 1/1994 | Tsai |
| 5,288,531 A | 2/1994 | Falla et al. |
| 5,288,560 A | 2/1994 | Sudo et al. |
| 5,288,799 A | 2/1994 | Schmidt et al. |
| 5,290,856 A | 3/1994 | Okamoto |
| 5,292,306 A | 3/1994 | Wynkoop et al. |
| 5,294,763 A | 3/1994 | Chamberlain et al. |
| 5,302,093 A | 4/1994 | Owens et al. |
| 5,306,542 A | 4/1994 | Bayer |
| 5,312,867 A | 5/1994 | Mitsuno et al. |
| 5,316,452 A | 5/1994 | Bogen et al. |
| 5,317,059 A | 5/1994 | Chundury et al. |
| 5,322,519 A | 6/1994 | Ash |
| 5,331,057 A | 7/1994 | Brekner et al. |
| 5,332,372 A | 7/1994 | Reynolds |
| 5,334,139 A | 8/1994 | Jeppsson et al. |
| 5,336,171 A | 8/1994 | Folden |
| 5,336,173 A | 8/1994 | Folden |
| 5,336,190 A | 8/1994 | Moss et al. |
| 5,338,293 A | 8/1994 | Jeppsson et al. |
| 5,342,886 A | 8/1994 | Glotin et al. |
| 5,344,292 A | 9/1994 | Rabenau et al. |
| 5,346,471 A | 9/1994 | Raulerson |
| 5,348,794 A | 9/1994 | Takahashi |
| 5,350,357 A | 9/1994 | Kamen et al. |
| 5,350,358 A | 9/1994 | Martin |
| 5,356,676 A | 10/1994 | Von Widdern et al. |
| 5,359,001 A | 10/1994 | Epple et al. |
| 5,360,648 A | 11/1994 | Falla et al. |
| 5,364,344 A | 11/1994 | Beattie et al. |
| 5,364,371 A | 11/1994 | Kamen |
| 5,364,486 A | 11/1994 | Falla et al. |
| 5,371,151 A | 12/1994 | Berge et al. |
| 5,378,126 A | 1/1995 | Abrahamson et al. |
| 5,378,230 A | 1/1995 | Mahurkar |
| 5,378,543 A | 1/1995 | Muruta et al. |
| 5,378,800 A | 1/1995 | Mok et al. |
| 5,380,276 A | 1/1995 | Miller et al. |
| 5,382,630 A | 1/1995 | Stehling et al. |
| 5,382,631 A | 1/1995 | Stehling et al. |
| 5,385,540 A | 1/1995 | Abbott et al. |
| 5,387,645 A | 2/1995 | Montag et al. |
| 5,389,243 A | 2/1995 | Kaplan |
| 5,397,222 A | 3/1995 | Moss et al. |
| 5,399,646 A | 3/1995 | Kohara et al. |
| 5,401,238 A | 3/1995 | Pirazzoli |
| 5,401,342 A | 3/1995 | Vincent et al. |
| 5,409,355 A | 4/1995 | Brooke |
| 5,415,528 A | 5/1995 | Ogden et al. |
| 5,421,208 A | 6/1995 | Packard et al. |
| 5,421,814 A | 6/1995 | Geary |
| 5,421,823 A | 6/1995 | Kamen et al. |
| 5,422,409 A | 6/1995 | Brekner et al. |
| 5,423,768 A | 6/1995 | Folden et al. |
| 5,427,509 A | 6/1995 | Chapman et al. |
| 5,429,485 A | 7/1995 | Dodge |
| 5,431,626 A | 7/1995 | Bryant et al. |
| 5,433,588 A | 7/1995 | Monk et al. |
| 5,438,510 A | 8/1995 | Bryant et al. |
| 5,439,587 A | 8/1995 | Stankowski et al. |
| 5,442,919 A | 8/1995 | Wilhelm |
| 5,445,506 A | 8/1995 | Afflerbaugh et al. |
| 5,445,610 A | 8/1995 | Peabody |
| 5,446,270 A | 8/1995 | Chamberlain et al. |
| 5,457,249 A | 10/1995 | Sagane et al. |
| 5,458,468 A | 10/1995 | Ye et al. |
| 5,460,490 A | 10/1995 | Carr et al. |
| 5,460,493 A | 10/1995 | Deniega et al. |
| 5,462,416 A | 10/1995 | Dennehy et al. |
| 5,464,388 A | 11/1995 | Merte et al. |
| 5,464,398 A | 11/1995 | Haindl |
| 5,474,683 A | 12/1995 | Bryant et al. |
| 5,475,060 A | 12/1995 | Brekner et al. |
| 5,476,368 A | 12/1995 | Rabenau et al. |
| 5,480,294 A | 1/1996 | Di Perna et al. |
| 5,482,438 A | 1/1996 | Anderson et al. |
| 5,482,440 A | 1/1996 | Dennehey et al. |
| 5,482,770 A | 1/1996 | Bekele |
| 5,484,404 A | 1/1996 | Schulman et al. |
| 5,487,649 A | 1/1996 | Dorsey, III et al. |
| 5,498,338 A | 3/1996 | Kruger et al. |
| 5,498,677 A | 3/1996 | Weller |
| 5,508,051 A | 4/1996 | Falla et al. |
| 5,514,102 A | 5/1996 | Winterer et al. |
| 5,518,378 A | 5/1996 | Neftel et al. |
| 5,522,769 A | 6/1996 | DeGuiseppi |

(56) References Cited

U.S. PATENT DOCUMENTS

| | | |
|---|---|---|
| 5,525,659 A | 6/1996 | Falla et al. |
| 5,526,844 A | 6/1996 | Kamen |
| 5,527,274 A | 6/1996 | Zakko |
| 5,529,708 A | 6/1996 | Palmgren et al. |
| 5,530,065 A | 6/1996 | Farley et al. |
| 5,533,389 A | 7/1996 | Kamen et al. |
| 5,534,606 A | 7/1996 | Bennett et al. |
| 5,536,412 A | 7/1996 | Ash |
| 5,540,568 A | 7/1996 | Rosen et al. |
| 5,540,808 A | 7/1996 | Vincent et al. |
| 5,542,919 A | 8/1996 | Simon et al. |
| 5,552,504 A | 9/1996 | Bennett et al. |
| 5,554,013 A | 9/1996 | Owens et al. |
| 5,556,263 A | 9/1996 | Jacobsen et al. |
| 5,569,026 A | 10/1996 | Novak |
| 5,569,182 A | 10/1996 | Twardowski et al. |
| 5,570,716 A | 11/1996 | Kamen et al. |
| 5,575,310 A | 11/1996 | Kamen et al. |
| 5,575,632 A | 11/1996 | Morris et al. |
| 5,578,012 A | 11/1996 | Kamen et al. |
| 5,580,460 A | 12/1996 | Polaschegg |
| 5,580,914 A | 12/1996 | Falla et al. |
| 5,583,192 A | 12/1996 | Bennett et al. |
| 5,586,868 A | 12/1996 | Lawless et al. |
| 5,588,815 A | 12/1996 | Zaleski, II |
| 5,588,816 A | 12/1996 | Abbott et al. |
| 5,591,344 A | 1/1997 | Kenley et al. |
| 5,601,420 A | 2/1997 | Warner et al. |
| 5,603,354 A | 2/1997 | Jacobsen et al. |
| 5,609,572 A | 3/1997 | Lang |
| 5,610,253 A | 3/1997 | Hatke et al. |
| 5,620,312 A | 4/1997 | Hyman et al. |
| 5,620,425 A | 4/1997 | Hefferman et al. |
| 5,628,908 A | 5/1997 | Kamen et al. |
| 5,629,398 A | 5/1997 | Okamoto et al. |
| 5,630,935 A | 5/1997 | Treu |
| 5,632,606 A | 5/1997 | Jacobsen et al. |
| 5,634,896 A | 6/1997 | Bryant et al. |
| 5,637,100 A | 6/1997 | Sudo |
| 5,637,400 A | 6/1997 | Brekner et al. |
| 5,641,405 A | 6/1997 | Keshaviah et al. |
| 5,643,201 A | 7/1997 | Peabody et al. |
| 5,645,734 A | 7/1997 | Kenley et al. |
| 5,650,471 A | 7/1997 | Abe et al. |
| 5,655,897 A | 8/1997 | Neftel et al. |
| 5,669,764 A | 9/1997 | Behringer et al. |
| 5,674,944 A | 10/1997 | Falla et al. |
| 5,676,530 A | 10/1997 | Nazarifar |
| 5,685,867 A | 11/1997 | Twardowski et al. |
| 5,686,527 A | 11/1997 | Laurin et al. |
| 5,693,728 A | 12/1997 | Okamoto et al. |
| 5,698,645 A | 12/1997 | Weller et al. |
| 5,698,654 A | 12/1997 | Nye et al. |
| 5,707,751 A | 1/1998 | Garza et al. |
| 5,711,654 A | 1/1998 | Afflerbaugh |
| 5,718,569 A | 2/1998 | Holst |
| 5,718,692 A | 2/1998 | Schon et al. |
| 5,721,025 A | 2/1998 | Falla et al. |
| 5,722,947 A | 3/1998 | Jeppsson et al. |
| 5,723,189 A | 3/1998 | Sudo |
| 5,733,991 A | 3/1998 | Rohrman et al. |
| 5,741,125 A | 4/1998 | Neftel et al. |
| 5,744,664 A | 4/1998 | Brekner et al. |
| 5,752,813 A | 5/1998 | Tyner et al. |
| 5,756,623 A | 5/1998 | Krueder et al. |
| 5,758,563 A | 6/1998 | Robinson |
| 5,776,111 A | 7/1998 | Tesio |
| 5,782,575 A | 7/1998 | Vincent et al. |
| 5,783,072 A | 7/1998 | Kenley et al. |
| 5,788,670 A | 8/1998 | Reinhard et al. |
| 5,788,671 A | 8/1998 | Johnson |
| 5,788,680 A | 8/1998 | Linder |
| 5,790,752 A | 8/1998 | Anglin et al. |
| 5,792,824 A | 8/1998 | Natori |
| 5,795,326 A | 8/1998 | Simán |
| 5,795,945 A | 8/1998 | Natori |
| 5,807,075 A | 9/1998 | Jacobsen et al. |
| 5,807,311 A | 9/1998 | Palestrant |
| 5,814,004 A | 9/1998 | Tamari |
| 5,816,779 A | 10/1998 | Lawless et al. |
| 5,836,908 A | 11/1998 | Beden et al. |
| 5,849,843 A | 12/1998 | Laurin et al. |
| 5,854,347 A | 12/1998 | Laurin et al. |
| 5,854,349 A | 12/1998 | Abe et al. |
| 5,863,986 A | 1/1999 | Herrmann-Schonherr et al. |
| 5,871,566 A | 2/1999 | Rutz |
| 5,872,201 A | 2/1999 | Cheung et al. |
| 5,879,768 A | 3/1999 | Falla et al. |
| 5,899,674 A | 5/1999 | Jung et al. |
| 5,906,598 A | 5/1999 | Giesler et al. |
| 5,919,369 A | 7/1999 | Ash |
| 5,921,951 A | 7/1999 | Morris |
| 5,924,975 A | 7/1999 | Goldowsky |
| 5,925,011 A | 7/1999 | Faict et al. |
| 5,927,956 A | 7/1999 | Lim et al. |
| 5,928,196 A | 7/1999 | Johnson et al. |
| 5,931,647 A | 8/1999 | Jacobsen et al. |
| 5,931,808 A | 8/1999 | Pike |
| 5,931,829 A | 8/1999 | Burbank et al. |
| 5,938,634 A | 8/1999 | Packard |
| 5,942,579 A | 8/1999 | Falla et al. |
| 5,944,495 A | 8/1999 | Jacobsen et al. |
| 5,944,684 A | 8/1999 | Roberts et al. |
| 5,945,187 A | 8/1999 | Buch-Rasmussen et al. |
| 5,947,953 A | 9/1999 | Ash et al. |
| 5,961,486 A | 10/1999 | Twardowski et al. |
| 5,964,796 A | 10/1999 | Imran |
| 5,965,433 A | 10/1999 | Gardetto et al. |
| 5,968,009 A | 10/1999 | Simán |
| 5,976,103 A | 11/1999 | Martin |
| 5,980,481 A | 11/1999 | Gorsuch |
| 5,980,495 A | 11/1999 | Heinz et al. |
| 5,983,136 A | 11/1999 | Kamen |
| 5,984,762 A | 11/1999 | Tedeschi et al. |
| 5,989,206 A | 11/1999 | Prosl et al. |
| 5,989,423 A | 11/1999 | Kamen et al. |
| 5,990,254 A | 11/1999 | Weller et al. |
| 5,993,949 A | 11/1999 | Rosenbaum et al. |
| 5,998,019 A | 12/1999 | Rosenbaum et al. |
| 6,001,078 A | 12/1999 | Reekers |
| 6,001,079 A | 12/1999 | Pourchez |
| 6,001,201 A | 12/1999 | Vincent et al. |
| 6,007,310 A | 12/1999 | Jacobsen et al. |
| 6,007,520 A | 12/1999 | Sudo |
| 6,017,194 A | 1/2000 | North, Jr. |
| 6,020,444 A | 2/2000 | Riedel et al. |
| 6,030,359 A | 2/2000 | Nowosielski |
| 6,036,458 A | 3/2000 | Cole et al. |
| 6,036,668 A | 3/2000 | Mathis |
| 6,041,801 A | 3/2000 | Gray et al. |
| 6,045,648 A | 4/2000 | Palmgren et al. |
| 6,048,329 A | 4/2000 | Thompson et al. |
| 6,056,522 A | 5/2000 | Johnson |
| 6,059,544 A | 5/2000 | Jung et al. |
| 6,060,572 A | 5/2000 | Gillis et al. |
| 6,065,270 A | 5/2000 | Reinhard et al. |
| 6,065,941 A | 5/2000 | Gray et al. |
| 6,068,936 A | 5/2000 | Pfeiffer et al. |
| 6,070,761 A | 6/2000 | Bloom et al. |
| 6,074,183 A | 6/2000 | Allen et al. |
| 6,074,359 A | 6/2000 | Keshaviah et al. |
| 6,074,374 A | 6/2000 | Fulton |
| 6,077,246 A | 6/2000 | Kullas et al. |
| 6,106,948 A | 8/2000 | Wang et al. |
| 6,109,895 A | 8/2000 | Ray et al. |
| 6,110,549 A | 8/2000 | Hamada et al. |
| 6,110,617 A | 8/2000 | Feres |
| 6,111,019 A | 8/2000 | Arjunan et al. |
| 6,114,457 A | 9/2000 | Markel et al. |
| 6,117,106 A | 9/2000 | Wasicek et al. |
| 6,117,465 A | 9/2000 | Falla et al. |
| 6,121,394 A | 9/2000 | Sugimoto et al. |
| 6,126,403 A | 10/2000 | Yamada |
| 6,126,631 A | 10/2000 | Loggie |

(56) References Cited

U.S. PATENT DOCUMENTS

| | | | |
|---|---|---|---|
| 6,129,699 A | 10/2000 | Haight et al. |
| 6,132,405 A | 10/2000 | Nilsson et al. |
| 6,136,744 A | 10/2000 | Gillis et al. |
| 6,146,354 A | 11/2000 | Beil |
| 6,147,025 A | 11/2000 | Gillis et al. |
| 6,149,621 A | 11/2000 | Makihara |
| 6,156,016 A | 12/2000 | Maginot |
| 6,159,195 A | 12/2000 | Ha et al. |
| 6,165,154 A | 12/2000 | Gray et al. |
| 6,168,862 B1 | 1/2001 | Rosenbaum et al. |
| 6,169,052 B1 | 1/2001 | Brekner et al. |
| 6,171,670 B1 | 1/2001 | Sudo et al. |
| 6,186,752 B1 | 2/2001 | Deniega et al. |
| 6,189,195 B1 | 2/2001 | Reilly et al. |
| 6,190,349 B1 | 2/2001 | Ash et al. |
| 6,190,371 B1 | 2/2001 | Maginot et al. |
| 6,191,254 B1 | 2/2001 | Falla et al. |
| 6,193,684 B1 | 2/2001 | Burbank et al. |
| 6,203,296 B1 | 3/2001 | Ray et al. |
| 6,206,849 B1 | 3/2001 | Martin et al. |
| 6,208,107 B1 | 3/2001 | Maske et al. |
| 6,210,361 B1 | 4/2001 | Kamen et al. |
| 6,221,648 B1 | 4/2001 | La Page et al. |
| 6,223,130 B1 | 4/2001 | Gray et al. |
| 6,225,426 B1 | 5/2001 | Gillis et al. |
| 6,225,427 B1 | 5/2001 | Burton et al. |
| 6,228,047 B1 | 5/2001 | Dadson |
| 6,231,320 B1 | 5/2001 | Lawless et al. |
| 6,234,991 B1 | 5/2001 | Gorsuch |
| 6,234,997 B1 | 5/2001 | Kamen et al. |
| RE37,208 E | 6/2001 | Winter et al. |
| 6,245,039 B1 | 6/2001 | Brugger et al. |
| 6,248,092 B1 | 6/2001 | Miraki et al. |
| 6,248,093 B1 | 6/2001 | Moberg |
| 6,254,567 B1 | 7/2001 | Treu et al. |
| 6,255,396 B1 | 7/2001 | Ding et al. |
| 6,258,079 B1 | 7/2001 | Burbank et al. |
| 6,261,655 B1 | 7/2001 | Rosenbaum et al. |
| 6,266,664 B1 | 7/2001 | Russell-Falla et al. |
| 6,270,673 B1 | 8/2001 | Belt et al. |
| 6,280,408 B1 | 8/2001 | Sipin |
| 6,280,423 B1 | 8/2001 | Davey et al. |
| 6,290,669 B1 | 9/2001 | Zicherman |
| 6,293,926 B1 | 9/2001 | Sorensen et al. |
| 6,302,653 B1 | 10/2001 | Bryant et al. |
| 6,302,875 B1 | 10/2001 | Makower et al. |
| 6,331,174 B1 | 12/2001 | Reinhard et al. |
| 6,343,614 B1 | 2/2002 | Gray et al. |
| 6,364,857 B1 | 4/2002 | Gray et al. |
| 6,372,848 B1 | 4/2002 | Yang et al. |
| 6,382,923 B1 | 5/2002 | Gray |
| 6,409,699 B1 | 6/2002 | Ash |
| 6,416,293 B1 | 7/2002 | Bouchard |
| 6,484,383 B1 | 11/2002 | Herklotz |
| 6,491,656 B1 | 12/2002 | Morris |
| 6,491,658 B1 | 12/2002 | Miura et al. |
| 6,497,676 B1 | 12/2002 | Childers et al. |
| 6,503,062 B1 | 1/2003 | Gray et al. |
| 6,542,761 B1 | 4/2003 | Jahn et al. |
| 6,555,058 B2 | 4/2003 | Kamibayashi et al. |
| 6,558,340 B1 | 5/2003 | Traeger |
| 6,561,996 B1 | 5/2003 | Gorsuch |
| 6,561,997 B1 | 5/2003 | Weitzel et al. |
| 6,585,681 B2 | 7/2003 | Brugger et al. |
| 6,585,682 B1 | 7/2003 | Haraldsson et al. |
| 6,592,542 B2 | 7/2003 | Childers et al. |
| 6,595,948 B2 | 7/2003 | Suzuki et al. |
| 6,666,842 B1 | 12/2003 | Sakai |
| 6,672,841 B1 | 1/2004 | Herklotz et al. |
| 6,719,733 B1 | 4/2004 | Heffernan et al. |
| 6,743,201 B1 | 6/2004 | Dönig et al. |
| 6,752,172 B2 | 6/2004 | Lauer |
| 6,758,975 B2 | 7/2004 | Peabody et al. |
| 6,808,369 B2 | 10/2004 | Grey et al. |
| 6,814,547 B2 | 11/2004 | Childers et al. |
| 6,869,538 B2 | 3/2005 | Yu et al. |
| 6,948,918 B2 | 9/2005 | Hansen |
| 6,949,079 B1 | 9/2005 | Westberg et al. |
| 6,964,917 B2 | 11/2005 | Tsvetkov et al. |
| 7,004,924 B1 | 2/2006 | Brugger et al. |
| 7,107,837 B2 | 9/2006 | Lauman et al. |
| 7,153,286 B2 | 12/2006 | Busby et al. |
| 7,208,092 B2 | 4/2007 | Micheli |
| 7,228,160 B2 | 6/2007 | Haight et al. |
| 7,238,164 B2 | 7/2007 | Childers et al. |
| 7,264,616 B2 | 9/2007 | Shehada et al. |
| 7,303,541 B2 | 12/2007 | Hamada et al. |
| 7,311,690 B2 | 12/2007 | Burnett |
| 7,354,417 B1 | 4/2008 | Levin et al. |
| 7,381,190 B2 | 6/2008 | Sugrue et al. |
| 7,503,915 B2 | 3/2009 | Beden et al. |
| 7,842,002 B2 | 11/2010 | Mantle |
| 7,867,214 B2 | 1/2011 | Childers et al. |
| 7,957,927 B2 | 6/2011 | Huitt et al. |
| 7,981,281 B2 | 7/2011 | Yu et al. |
| 7,988,686 B2 | 8/2011 | Beden et al. |
| 8,180,574 B2 | 5/2012 | Lo et al. |
| 8,187,250 B2 | 5/2012 | Roberts et al. |
| 8,197,439 B2 | 6/2012 | Wang et al. |
| 8,202,248 B2 | 6/2012 | Burnett et al. |
| 8,226,595 B2 | 7/2012 | Childers et al. |
| 8,298,170 B2 | 10/2012 | Lundtveit et al. |
| 8,323,231 B2 | 12/2012 | Childers et al. |
| 8,376,999 B2 | 2/2013 | Busby et al. |
| 8,439,960 B2 | 5/2013 | Burnett et al. |
| 8,496,609 B2 | 7/2013 | Childers et al. |
| 8,512,553 B2 | 8/2013 | Cicchello et al. |
| 8,585,635 B2 | 11/2013 | Degen et al. |
| 8,597,229 B2 | 12/2013 | Pan |
| 8,641,659 B2 | 2/2014 | Soykan et al. |
| 8,672,884 B2 | 3/2014 | Burnett et al. |
| 8,702,985 B2 | 4/2014 | Sebesta et al. |
| 8,721,883 B2 | 5/2014 | Lauer |
| 8,801,652 B2 | 8/2014 | Landherr et al. |
| 8,841,117 B2 | 9/2014 | Nagai et al. |
| 8,869,612 B2 | 10/2014 | Chen et al. |
| 8,992,461 B2 | 3/2015 | Hedmann et al. |
| 9,039,652 B2 | 5/2015 | Degen et al. |
| 9,066,968 B2 | 6/2015 | Ohta et al. |
| 9,101,707 B2 | 8/2015 | Zeltser et al. |
| 9,147,045 B2 | 9/2015 | Yu et al. |
| 9,204,828 B2 | 12/2015 | Burnett et al. |
| 9,320,842 B2 | 4/2016 | Orhan et al. |
| 9,440,017 B2 | 9/2016 | Rohde et al. |
| 9,514,283 B2 | 12/2016 | Childers et al. |
| 9,579,443 B2 | 2/2017 | Plahey et al. |
| 9,603,558 B2 | 3/2017 | Burnett et al. |
| 9,662,058 B2 | 5/2017 | Burnett et al. |
| 9,827,361 B2 | 11/2017 | Pudil et al. |
| 9,861,732 B2 | 1/2018 | Scarpaci et al. |
| 2001/0014793 A1 | 8/2001 | Brugger et al. |
| 2001/0018937 A1 | 9/2001 | Nemoto |
| 2001/0034502 A1 | 10/2001 | Moberg et al. |
| 2002/0041825 A1 | 4/2002 | Scheunert et al. |
| 2002/0045851 A1 | 4/2002 | Suzuki et al. |
| 2002/0062109 A1 | 5/2002 | Lauer |
| 2002/0077598 A1 | 6/2002 | Yap et al. |
| 2003/0012905 A1 | 1/2003 | Zumbrum et al. |
| 2003/0100882 A1 | 5/2003 | Beden et al. |
| 2003/0195454 A1 | 10/2003 | Wariar et al. |
| 2003/0204162 A1 | 10/2003 | Childers et al. |
| 2003/0220599 A1* | 11/2003 | Lundtveit ............. A61M 1/288 604/5.01 |
| 2003/0220600 A1 | 11/2003 | Gotch et al. |
| 2004/0115068 A1 | 6/2004 | Hansen et al. |
| 2004/0124147 A1* | 7/2004 | Fissell, IV ......... B01D 67/0088 210/650 |
| 2004/0254513 A1 | 12/2004 | Shang et al. |
| 2005/0118038 A1 | 6/2005 | Grey et al. |
| 2005/0221314 A1 | 10/2005 | Berlin et al. |
| 2006/0113249 A1* | 6/2006 | Childers ................ A61M 1/28 210/645 |
| 2006/0189923 A1 | 8/2006 | Neftel et al. |
| 2006/0195064 A1 | 8/2006 | Plahey et al. |

(56) References Cited

U.S. PATENT DOCUMENTS

| | | |
|---|---|---|
| 2008/0299467 A1 | 12/2008 | Kim et al. |
| 2009/0216211 A1 | 8/2009 | Beden et al. |
| 2010/0051552 A1 | 3/2010 | Rohde et al. |
| 2010/0280435 A1* | 11/2010 | Raney ............. A61F 9/00745 604/22 |
| 2010/0312174 A1 | 12/2010 | Hoffman |
| 2014/0018727 A1 | 1/2014 | Burbank et al. |
| 2014/0099617 A1 | 4/2014 | Tallman, Jr. |
| 2014/0303455 A1 | 10/2014 | Shachar et al. |
| 2015/0133854 A1 | 5/2015 | Zhu et al. |
| 2015/0253321 A1 | 9/2015 | Chou et al. |
| 2016/0082200 A1 | 3/2016 | Lauer et al. |
| 2016/0101226 A1 | 4/2016 | Beiriger |
| 2016/0183819 A1 | 6/2016 | Burnett et al. |
| 2017/0072125 A1 | 3/2017 | Wallenas et al. |
| 2017/0157311 A1 | 6/2017 | Egley |
| 2017/0203083 A1 | 7/2017 | Chappel |
| 2017/0281062 A1 | 10/2017 | Burnett et al. |
| 2017/0281846 A1 | 10/2017 | Manda et al. |
| 2017/0281847 A1 | 10/2017 | Manda et al. |
| 2017/0281848 A1 | 10/2017 | Axelsson et al. |
| 2017/0319769 A1 | 11/2017 | Wieslander et al. |
| 2017/0347926 A1 | 12/2017 | Farooqui |
| 2017/0367646 A1 | 12/2017 | Schmidt et al. |
| 2017/0368248 A1 | 12/2017 | Neftel et al. |
| 2017/0368249 A1 | 12/2017 | Bourne |
| 2018/0001009 A1 | 1/2018 | Crawford et al. |

FOREIGN PATENT DOCUMENTS

| | | |
|---|---|---|
| DE | 251 904 A3 | 12/1987 |
| DE | 3739556 A1 | 6/1989 |
| DE | 39 37 865 A1 | 6/1990 |
| DE | 19837667 | 3/2000 |
| DE | 19929572 | 11/2000 |
| DE | 10034711 | 2/2002 |
| DE | 10039196 | 2/2002 |
| DE | 10042324 | 2/2002 |
| DE | 10053441 | 5/2002 |
| DE | 10157924 | 6/2003 |
| DE | 10224750 | 12/2003 |
| EP | 0028371 | 5/1981 |
| EP | 0 033 096 | 8/1981 |
| EP | 0 052 004 | 5/1982 |
| EP | 0 097 432 | 1/1984 |
| EP | 0 156 464 A1 | 10/1985 |
| EP | 0 157 024 | 10/1985 |
| EP | 0 206 195 | 11/1986 |
| EP | 0204260 | 12/1986 |
| EP | 0 306 664 A2 | 3/1989 |
| EP | 0319272 | 6/1989 |
| EP | 0 333 308 B1 | 9/1989 |
| EP | 0 381 042 A1 | 8/1990 |
| EP | 0402505 | 12/1990 |
| EP | 0410125 | 1/1991 |
| EP | 0 535 874 B1 | 4/1993 |
| EP | 0 554 722 A1 | 8/1993 |
| EP | 0619135 | 10/1994 |
| EP | 0 283 164 B1 | 5/1995 |
| EP | 0 492 982 B1 | 8/1995 |
| EP | 0 684 845 B1 | 12/1995 |
| EP | 0 430 585 B1 | 1/1996 |
| EP | 0 156 464 B1 | 5/1996 |
| EP | 0 582 355 B1 | 5/1996 |
| EP | 0 709 105 A1 | 5/1996 |
| EP | 0 660 725 | 7/1996 |
| EP | 0 203 799 B1 | 8/1996 |
| EP | 0 384 694 B1 | 9/1996 |
| EP | 0 497 567 B1 | 9/1996 |
| EP | 0 291 208 B1 | 8/1997 |
| EP | 0 790 063 A1 | 8/1997 |
| EP | 0 680 401 B1 | 1/1999 |
| EP | 0947814 | 10/1999 |
| EP | 0956876 | 11/1999 |
| EP | 1 110 564 A2 | 6/2001 |
| EP | 1 110 565 A2 | 6/2001 |
| EP | 0 709 105 B1 | 12/2001 |
| EP | 0957954 | 5/2003 |
| EP | 1314443 | 5/2003 |
| EP | 1403519 | 3/2004 |
| EP | 1546556 | 12/2006 |
| EP | 1754890 | 2/2007 |
| EP | 2168612 | 3/2010 |
| EP | 2623139 | 8/2013 |
| EP | 2814537 | 5/2017 |
| FR | 2371931 | 6/1978 |
| FR | 2440740 | 6/1980 |
| GB | 1326236 | 8/1973 |
| PT | 1201264 | 10/2001 |
| SE | 331736 | 1/1985 |
| WO | WO 86/01115 | 2/1968 |
| WO | WO 84/02473 | 7/1984 |
| WO | WO 85/04813 | 11/1985 |
| WO | 89/01795 | 3/1986 |
| WO | 87/05223 | 9/1986 |
| WO | WO 88/03389 | 5/1988 |
| WO | 90/13795 | 11/1990 |
| WO | WO 93/01845 | 2/1993 |
| WO | 94/20158 | 9/1994 |
| WO | WO 95/35124 | 12/1995 |
| WO | WO 97/08054 | 3/1997 |
| WO | WO 98/17333 | 4/1998 |
| WO | WO 98/22167 | 5/1998 |
| WO | WO 98/27926 | 7/1998 |
| WO | WO 98/44043 | 10/1998 |
| WO | WO 98/50088 | 11/1998 |
| WO | WO 99/06082 | 2/1999 |
| WO | WO 99/07301 | 2/1999 |
| WO | WO 99/48990 | 9/1999 |
| WO | WO 99/06082 | 11/1999 |
| WO | WO 00/10385 | 3/2000 |
| WO | WO 00/20050 | 4/2000 |
| WO | WO 01/58509 A1 | 8/2001 |
| WO | WO 2004/029457 | 4/2004 |
| WO | 2008086619 | 1/2008 |
| WO | 2009094035 | 7/2009 |
| WO | 2013122580 | 8/2013 |
| WO | 2017034452 | 3/2017 |
| WO | 2017062923 | 4/2017 |

* cited by examiner

SYSTEMS AND METHODS FOR INCORPORATING PATIENT PRESSURE INTO MEDICAL FLUID DELIVERY

BACKGROUND

The present disclosure relates generally to medical fluid delivery machines and more particularly to patient pressure measurements taken in connection with medical fluid delivery.

One type of medical fluid delivery pertinent to the present disclosure is medical fluid delivery that treats kidney failure. Due to various causes, a person's renal system can fail. Renal failure produces several physiological derangements. For example, it is no longer possible to balance water and minerals or to excrete daily metabolic load. Toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that normal functioning kidneys would otherwise remove. One type of dialysis treatment is peritoneal dialysis, which infuses a dialysis solution, also called dialysis fluid, into a patient's peritoneal cavity via a catheter. The dialysis fluid contacts the peritoneal membrane of the peritoneal cavity. Waste, toxins and excess water pass from the patient's bloodstream, through the peritoneal membrane and into the dialysis fluid due to diffusion and osmosis, i.e., an osmotic gradient occurs across the membrane. An osmotic agent in dialysis provides the osmotic gradient. The used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), and tidal flow dialysis and continuous flow peritoneal dialysis ("CFPD"). CAPD is a manual dialysis treatment. Here, the patient manually connects an implanted catheter to a drain to allow used or spent dialysate fluid to drain from the peritoneal cavity. The patient then connects the catheter to a bag of fresh dialysis fluid to infuse fresh dialysis fluid through the catheter and into the patient. The patient disconnects the catheter from the fresh dialysis fluid bag and allows the dialysis fluid to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to perform the treatment cycles manually and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal cavity. APD machines also allow for the dialysis fluid to dwell within the cavity and for the transfer of waste, toxins and excess water to take place. The source may include multiple sterile dialysis fluid bags.

APD machines pump used or spent dialysate from the peritoneal cavity, though the catheter, and to the drain. As with the manual process, several drain, fill and dwell cycles occur during APD. A "last fill" occurs at the end of APD and remains in the peritoneal cavity of the patient until the next treatment. The dialysis fluid is typically "cycled" (filled, dwelled and drained) four to five times over a treatment, e.g., nightly treatment. Typical fill volumes vary due to several clinical factors but may average about 2.0 to 2.5 liters.

One problem with APD machines is that although the machines record and therefore know how much fluid has been delivered to the patient and removed from the patient, the APD machine does not actually know how much dialysis fluid is left within the patient at the end of a drain. That is, the machine may think its has completely drained the patient but there may still be some residual volume left in the patient's peritoneal cavity. The primary reason for this is that the amount of ultrafiltration ("UF") removed from the patient is a variable with peritoneal dialysis, and not a controlled amount like with hemodialysis or other renal therapies. With PD, UF removed depends upon the osmotic capability of the solution used, the length of time that the solution is left to dwell within the patient's peritoneum, and the ability of the patient's peritoneal wall to transport UF into the peritoneum where it can be removed from the patient. It is therefore left to the doctor or clinician to predict how much UF will be removed over a dwell period of a cycle. For example, the doctor or clinician may predict that the amount of UF generated over a dwell will be seven percent of the fill volume. But the actual UF volume will likely be more or less than the exact seven percent calculation, leading to the uncertainty associated with patient draining.

Another factor involved with the uncertainty includes exchanges, such as midday exchanges, that are performed manually without the use of the APD machine. The first step in a treatment involving an APD machine is often a drain step to remove used peritoneal dialysis fluid that has resided within the patient over the course of the day. When a midday exchange is performed, the patient drains used fluid manually until the patient feels empty and then refills with fresh fluid. The amounts of the drain and refill are often not recorded and even if recorded, not entered into the APD machine. There is also a UF amount due to the refill, which adds to the uncertainty for the reasons discussed above. The result is that there is no way to precisely know how much daytime fluid the patient has to drain at the initial drain of the next a nighttime APD treatment. And the uncertainty of the initial drain leads to more uncertainty regarding how much fluid will reside within the patient at the end of each cycle.

Uncertainty with draining can lead to overfilling the patient on the next fill. Overfilling the patient may cause excessive pressure on the patient's diaphragm, blood vessels and internal organs, leading to patient discomfort and potentially adverse effects on cardiopulmonary function.

For the above reasons, a need exists for a better way to determine how much fluid resides within a patient to avoid overfilling and having a more accurate clinical understanding of how much spent dialysis fluid remains in the patient.

SUMMARY

The present disclosure sets forth systems and methods for pumping medical fluids to a patient, while preventing overfilling and over-pressurizing the patient. The present disclosure is set forth using peritoneal dialysis ("PD") as an example therapy that may benefit from the present systems and methods. It should be appreciated however that the present systems and methods are applicable to any type of medical fluid delivery in which a medical fluid is delivered to and collected in an area of the patient's body where pressure may build. Besides PD, the present systems and methods may also be applicable to medical fluid delivery, e.g., for drugs and/or nutritional fluids.

The present system and method measures pressure within the patient as fluid is being delivered to or removed from the patient. While controlling positive pressure and preventing overfilling are of one primary concern, it is also desired to be able to monitor and control negative pressure applied to the patient, e.g., during fluid removal, because too much negative pressure may also cause patient discomfort. In either case, it is contemplated that when the patient becomes full or empty, that a spike in positive or negative pressure will occur. When this pressure spike is sensed, pumping is stopped to prevent over-pressurizing (positive or negative) the patient.

In one primary embodiment, an APD machine uses positive pneumatic pressure to fill the patient. The APD includes a pump interface, which may include a pump actuation area for receiving positive and negative air pressure, positive pressure to fill the patient with fresh dialysis fluid and negative pressure to drain used dialysis fluid from the patient. A medical fluid handling device, such as a disposable cassette, is pressed up against the pump actuation area. The disposable cassette in an embodiment includes a fluid chamber that mates with the pneumatic actuation area of the pump interface. The chamber and actuation area are separated by a flexible membrane provided by the disposable cassette. Negative pneumatic pressure is applied to the pneumatic actuation area to pull the flexible membrane towards a wall of the area to in turn pull fluid into the fluid chamber. Positive pressure is applied to the actuation area to push the flexible membrane towards a wall of the fluid chamber to in turn push fluid from the fluid chamber towards the patient. The above process is repeated multiple times until a prescribed patient fill volume has been delivered to the patient.

The APD machine is under the control of a control unit. The control unit may include one or more processor, one or more memory, and one or more sub- or delegate controller. The control unit controls multiple valves of the APD machine, such as, pneumatic valves for (i) opening and closing the pneumatic chamber to atmosphere to vent the chamber, (ii) opening and closing the supply of positive pressure to the pneumatic chamber, (ii) opening and closing the supply of negative pressure to the pneumatic chamber, (iii) opening and closing a fluid line to the fluid chamber of the cassette and (iv) opening and closing a fluid line from the fluid chamber of the cassette to the patient. Certain of these valves may be repeated for a second pneumatic chamber of the pump interface and a mating second fluid chamber of the disposable cassette.

The control unit also receives pressure signal readings from multiple pressure sensors of the APD machine, such as, pneumatic pressure sensors positioned and arranged to read the pressure inside each of the pneumatic actuation areas of the pump interface of the APD machine. The pressure sensors may be configured for example to read in a range of 18 to 24 centimeters ("cm's") of water. Because the flexible membrane between the pneumatic actuation area and the fluid chamber is very thin, it may be assumed that the pressure measured in the pneumatic actuation area is equal to the pressure of the fluid in the fluid chamber of the cassette and the fluid lines (e.g., rigid cassette pathways and flexible tubes attached to the cassette) that are in fluid communication with the fluid chamber of the disposable cassette.

The control unit is programmed in an embodiment to periodically stop a pump-out stroke by closing a valve between the positive pressure source and the pneumatic chamber and to vent the pneumatic chamber to atmosphere by opening a valve in a vent line leading from the pneumatic chamber. When the pneumatic chamber is fully vented, the control unit closes the vent valve, so that the pneumatic chamber is now fully closed. The pneumatic chamber thereafter becomes pressurized by the fluid in the fluid chamber of the disposable cassette, the line leading from the disposable cassette to the patient, and the fluid in the peritoneal cavity of the patient. The resulting pressure when stabilized across the cassette, fluid line and peritoneal cavity represents the current patient pressure. The control unit takes one or more pressure readings at this time (e.g., multiple readings and averages them).

The present disclosure contemplates doing different things with the pressure reading. In one embodiment, the control unit compares the pressure reading with one or more pressure reading of one or more previous sequence. The control unit looks for a pressure spike or a change in the slope of a curve connecting the pressure readings, indicating that the peritoneal cavity is full. If no spike is sensed, pumping resumes. If the spike is sensed, the remainder of the fill is halted. This embodiment is advantageous because the pressure comparison is for a pressure change as opposed to comparing the pressure reading to a pressure limit, which may vary from patient to patient, for a given patient from treatment to treatment, or even during treatment due to a change in patient head height. In an alternative embodiment, the slope of pressure curve comparison may be combined with an upper pressure limit that, for example, is set high enough to be used with all patients for all treatments.

Pressure spikes may occur for reasons other than the patient being full. For example, the patient (who may be sleeping) may inadvertently kink a line, leading to a pressure spike. Or, the patient's catheter may be temporarily, partially blocked, again leading to a pressure spike. Further alternatively, the patient may change head height position relative to the medical fluid delivery machine or couch/bed during the measurement. To avoid halting the fill when the patient has not been completely filled even though a pressure spike is sensed, it is contemplated to program the control unit to reverse the pump to pull a known amount of dialysis fluid from the patient, e.g., one or more pump stroke(s) worth of fluid, and then re-reverse the pump to pump the same one or more pump stroke(s) back to the patient during which the pressure measurement sequence is performed again. Alternately, the pressure measurement may be monitored during both fluid removal and while refilling to confirm that the pressure spike disappears and then returns. If the pressure measurement again indicates that the patient is full, e.g., via the pressure spike or change in slope technique, then the remainder of the fill is halted. But if the pressure measurement does not indicate that the patient is full, the patient fill may continue knowing that the pressure measurement sequence will be performed again soon.

The control unit in one embodiment repeats the pressure measurement sequence periodically during a patient fill (or drain), e.g., once every 100 to 150 milliliters ("mL's") of dialysis fluid fill volume, wherein a full pump stroke may be around 20 mL's. The pressure measurement sequence may take about three to about thirty seconds, e.g., to fully vent, and then repressurize to the patient pressure (e.g., intraperitoneal pressure ("IPP")), upon which one or more pressure reading is recorded. In one embodiment, it is preferred to perform the pressure measurement sequence mid-stroke, as opposed to the end of a stroke where there already exists a slight pause, because the flexible membrane of the disposable cassette should be allowed to flex due to the patient pressure, yielding an accurate patient pressure reading in the pneumatic chamber, as opposed to being stuck against a wall of the fluid chamber or the pneumatic actuation area when at the end of stroke.

The control unit may alternatively compare the pressure reading with a pressure limit, and resume pumping if the measured pressure reading is within the pressure limit. The control unit halts the remainder of the fill if the measured pressure reading is outside the pressure limit. The pressure limit may be set based on a determined head height of the patient relative to the machine.

In a further alternative embodiment, the control unit compares the pressure reading with a pressure limit, resumes pumping if the measured pressure reading is within the pressure limit, and performs the above sequence one or more additional time if the measured pressure reading is outside the pressure limit. If the pressure reading is consistently outside the pressure limit over multiple sequences, the control unit halts the remainder of the fill.

The systems and methods of the present disclosure are not limited to pneumatic pumping or to the use of a disposable cassette. In another primary embodiment, an external pressure sensor apparatus is employed at a designated part of the medical fluid handling device, which may be a pump tubing set or a disposable cassette and associated fluid lines. Further alternatively, the external pressure sensor apparatus is associated with a PD patient's transfer set, which is the interface between a patient line of the fluid handling device and the patient's indwelling PD catheter. The external pressure sensor apparatus is considered external because it is not integrated within the medical fluid delivery machine itself. The pressure sensor apparatus is located instead on the inside of (i) the patient line, e.g., at its distal end, (ii) a disposable cassette, e.g., in a fluid pathway of the disposable cassette leading from the pump chambers to the patient port of the disposable cassette or the patient port itself, or (iii) the patient's transfer set. In each instance (i) to (iii), the sensor is positioned to contact fluid. The sensor apparatus may be powered by a small battery provided with the pressure sensor or have power leads that extend outside of the fluid handling device for receiving external power, e.g., from the medical fluid delivery machine.

The pressure sensor may be a micromechanical ("MEMS") type sensor found for example in mobile phones and wearable devices for elevation sensing. The sensor apparatus may be configured to communicate wirelessly with the medical fluid delivery machine. The medical fluid delivery machine may be configured such that upon detecting the presence of a fluid handling device, the medical fluid delivery machine automatically looks for a wireless signal. When the medical fluid delivery machine detects the signal, it may begin to take readings.

In one embodiment, the medical fluid delivery machine waits for a pause in the pumping to take a reading, which is then assumed to be a reading of the patient's pressure. In another embodiment, the medical fluid delivery machine reads the pressure sensor constantly or at regular intervals that are not synchronized with the pumping cycles. Here, the medical fluid delivery machine may be programmed to perform a signal analysis, such as a Fast Fourier Transform ("FFT"), on the reading in an attempt to decouple resonance frequency components and evaluate whether any of the components may indicate, or may be correlated to, patient pressure.

Regardless of how the external pressure sensor patient pressure readings are obtained, they may be analyzed as discussed above for the pneumatic pumping primary embodiment, e.g., compared to a limit or compared to themselves for a slope of curve or pressure spike analysis.

With either of the primary embodiments, it is contemplated to perform the patient pressure analysis once at the beginning of treatment. As discussed above, with APD it is difficult to know how much fluid resides within the patient when beginning the first patient fill. But once the first complete fill amount is established via the structures and methodology discussed herein, the patient's situation is better known. A fill/drain scheme may be developed from the sensed complete fill amount and be implemented going forward without performing the patient pressure analysis again. A programmed fill amount going forward of slightly less than the complete fill amount determined from the pressure sensing may be desirable to allow for a gain in volume over the dwell period due to UF. In an embodiment, a clinician or doctor may set an upper limit for the programmed fill amount that cannot be exceeded regardless of what the sensed complete fill amount dictates.

With either of the primary embodiments, it is contemplated to perform the patient pressure analysis alternatively at each fill and/or drain. As discussed above, the patient does not always drain completely. If an initial drain before the initial fill is incomplete, then the sensed complete fill amount will be less than if the patient had drained completely. It is therefore contemplated to program the next fill amount based on the previously sensed full fill amount taking into account UF that will accumulate over a dwell period. Again, in an embodiment, a clinician or doctor may set an upper limit for the programmed fill amount that cannot be exceeded regardless of what the sensed complete fill amount dictates.

In light of the disclosure herein and without limiting the disclosure in any way, in a first aspect of the present disclosure, which may be combined with any other aspect listed herein unless specified otherwise, a medical fluid delivery machine operating a medical fluid handling device, the medical fluid delivery machine includes: a pump interface including an actuation area for delivering positive pressure or negative pressure to the medical fluid handling device to move medical fluid into or out of the device, respectively, the medical fluid handling device capable of being placed in fluid communication with a patient; a pressure sensor positioned and arranged to measure pressure within the actuation area; a valve positioned and arranged to selectively vent the actuation area to atmosphere; and a control unit in signal communication with the pressure sensor and control communication with the valve, the control unit programmed to perform a sequence during pumping, wherein (i) application of positive pressure or negative pressure to the actuation area is stopped, the valve is switched to vent the actuation area to atmosphere, then switched to close the actuation area to atmosphere, and at least one pressure signal reading is taken via the pressure sensor, and (ii) a determination is made whether application of the positive pressure or negative pressure to the actuation area should be resumed based on the at least one pressure signal reading.

In a second aspect of the present disclosure, which may be combined with any other aspect listed herein unless specified otherwise, the control unit includes at least one of (i) at least one processor, (ii) at least one memory, or (iii) at least one delegate controller.

In a third aspect of the present disclosure, which may be combined with any other aspect listed herein unless specified otherwise, the valve is a first valve, and which includes a second valve under control of the control unit, the control unit further programmed so that in (i), stopping positive pressure or negative pressure to the actuation area includes switching the second valve to close the actuation area from a source of the positive or negative pressure and in (ii), resuming application of the positive pressure or negative pressure to the chamber includes switching the second valve to open the actuation area to the source of the positive or negative pressure.

In a fourth aspect of the present disclosure, which may be combined with the third aspect in combination with any other aspect listed herein unless specified otherwise, the pressure sensor is placed in fluid communication with a line leading from the source of the positive or negative pressure to the actuation area.

In a fifth aspect of the present disclosure, which may be combined with any other aspect listed herein unless specified otherwise, wherein during pumping includes during a pump stroke having a pump stroke beginning and a pump stroke end.

In a sixth aspect of the present disclosure, which may be combined with any other aspect listed herein unless specified otherwise, wherein the actuation area is a first actuation area and wherein the pump interface includes a second actuation area for delivering positive pressure or negative pressure to the medical fluid handling device to move medical fluid into or out of the device, and wherein the control unit is programmed to perform (i) and (ii) for both the first actuation area and the second actuation area.

In a seventh aspect of the present disclosure, which may be combined with any other aspect listed herein unless specified otherwise, wherein determining if application of the positive or negative pressure to the actuation area should be resumed includes the control unit being programmed to (iii) determine a difference between the at least one pressure signal and at least one pressure signal from at least one previous sequence.

In an eighth aspect of the present disclosure, which may be combined with the seventh aspect in combination with any other aspect listed herein unless specified otherwise, the control unit is programmed to (iv) resume pressure application if the pressure difference is at least substantially the same as a previously determined difference.

In a ninth aspect of the present disclosure, which may be combined with the seventh aspect in combination with any other aspect listed herein unless specified otherwise, the control unit is programmed to (iv) not resume pressure application if the pressure difference is different than a previously determined difference.

In a tenth aspect of the present disclosure, which may be combined with the ninth aspect in combination with any other aspect listed herein unless specified otherwise, the difference between the pressure differences is required to be at least a certain amount not to resume pressure application.

In an eleventh aspect of the present disclosure, which may be combined with the seventh aspect in combination with any other aspect listed herein unless specified otherwise, the control unit is programmed (iv) such that if the difference is different than a previously determined difference, at least one additional sequence is performed and pressure application is not resumed if a new difference is still different than the previously determined difference.

In a twelfth aspect of the present disclosure, which may be combined with the seventh aspect in combination with any other aspect listed herein unless specified otherwise, wherein the control unit is programmed (iv) such that if the difference is different than a previously determined difference, cause a reverse pumping of a medical fluid volume and then a re-reverse pumping of the medical fluid volume, and (v) perform (i) to (iii) again.

In a thirteenth aspect of the present disclosure, which may be combined with the twelfth aspect in combination with any other aspect listed herein unless specified otherwise, the control unit is programmed to not resume pressure application if the difference in (iii) performed again is still different than the previously determined difference.

In a fourteenth aspect of the present disclosure, which may be combined with the twelfth aspect in combination with any other aspect listed herein unless specified otherwise, the control unit is programmed to resume pressure application if the difference in (iii) performed again is at least substantially the same as the previously determined difference.

In a fifteenth aspect of the present disclosure, which may be combined with the twelfth aspect in combination with any other aspect listed herein unless specified otherwise, the sequence is for a patient fill in which positive pressure is applied in the actuation area, wherein the reverse pumping is a removal of the medical fluid volume from the patient and the re-reverse pumping is a return of the medical fluid volume to the patient, and wherein pressure within the actuation area is assumed to be pressure in the patient after the actuation area is vented to atmosphere and then closed to atmosphere.

In a sixteenth aspect of the present disclosure, which may be combined with the seventh aspect in combination with any other aspect listed herein unless specified otherwise, the control unit is programmed to apply a smoothing filter to multiple pressure difference determinations in looking for a change in pressure differences indicating that pressure application should not be resumed.

In a seventeenth aspect of the present disclosure, which may be combined with any other aspect listed herein unless specified otherwise, wherein determining if application of the positive pressure or negative pressure to the actuation area should be resumed includes determining if the at least one pressure signal reading is within a pressure limit.

In an eighteenth aspect of the present disclosure, which may be combined with the seventeenth aspect in combination with any other aspect listed herein unless specified otherwise, the control unit is programmed not to resume pressure application if the at least one pressure signal reading is outside the pressure limit.

In a nineteenth aspect of the present disclosure, which may be combined with any other aspect listed herein unless specified otherwise, a time duration for (i) to be completed is about three to about thirty seconds.

In a twentieth aspect of the present disclosure, which may be combined with any other aspect listed herein unless specified otherwise, the sequence is repeated during pumping in medical fluid volume increments.

In a twenty-first aspect of the present disclosure, any of the structure, functionality and alternatives discussed in connection with FIGS. 1 to 7 may be combined with any other aspect listed herein unless specified otherwise.

In a twenty-second aspect of the present disclosure, which may be combined with any other aspect listed herein unless specified otherwise, a medical fluid delivery system includes a medical fluid handling device including a patient line for being placed in fluid communication with a patient; and a medical fluid delivery machine including a pump actuator for actuating the medical fluid handling device to move medical fluid into or out of the device; a pressure sensor positioned and arranged within the medical fluid handling device so as to be able to sense pressure of the medical fluid; and a control unit in signal communication with the pressure sensor and control communication with the pump actuator, the control unit programmed during pumping to (i) determine if at least one signal reading or a component of the at least one signal reading from the pressure sensor is indicative of the pressure within the patient and (ii) determine from the at least one pressure signal reading or component reading indicative of the pressure in the patient whether to continue pumping or stop pumping.

In a twenty-third aspect of the present disclosure, which may be combined with the twenty-second aspect in combination with any other aspect listed herein unless specified otherwise, the medical fluid handling device further includes a patient transfer set for connecting to a patient's indwelling catheter, and wherein the pressure sensor is placed within the patient transfer set.

In a twenty-fourth aspect of the present disclosure, which may be combined with the twenty-second aspect in combination with any other aspect listed herein unless specified otherwise, the medical fluid handling device further includes a pumping cassette, and wherein the pressure sensor is placed within the pumping cassette.

In a twenty-fifth aspect of the present disclosure, which may be combined with the twenty-second aspect in combination with any other aspect listed herein unless specified otherwise, the pressure sensor is placed within the patient line.

In a twenty-sixth aspect of the present disclosure, which may be combined with the twenty-second aspect in combination with any other aspect listed herein unless specified otherwise, the pressure sensor is a micromechanical ("MEMS") sensor.

In a twenty-seventh aspect of the present disclosure, which may be combined with the twenty-second aspect in combination with any other aspect listed herein unless specified otherwise, the control unit is programmed to perform at least (i) or (ii) in a frequency domain.

In a twenty-eighth aspect of the present disclosure, which may be combined with the twenty-second aspect in combination with any other aspect listed herein unless specified otherwise, wherein determining from the at least one pressure signal reading or component of the at least one pressure signal reading whether to continue pumping or stop pumping includes evaluating a change in the at least one pressure signal reading or component of the at least one pressure signal reading.

In a twenty-ninth aspect of the present disclosure, any of the structure, functionality and alternatives discussed in connection with any one of FIGS. 1 to 7 may be combined with any of the structure, functionality and alternatives discussed in connection with any of the other of FIGS. 1 to 7 unless specified otherwise.

In light of the above discussion and aspects of the present disclosure, it is accordingly an advantage of the present disclosure to provide improved medical fluid delivery to a patient.

It is another advantage of the present disclosure to provide an improved automated peritoneal dialysis ("APD") treatment.

It is a further advantage of the present disclosure to improve patient comfort.

It is yet another advantage of the present disclosure to attempt to maximize fluid delivery volume while preventing patient overfilling.

The advantages discussed herein may be found in one, or some, and perhaps not all of the embodiments disclosed herein. Additional features and advantages are described herein, and will be apparent from the following Detailed Description and the figures.

DETAILED DESCRIPTION

Figure 1:
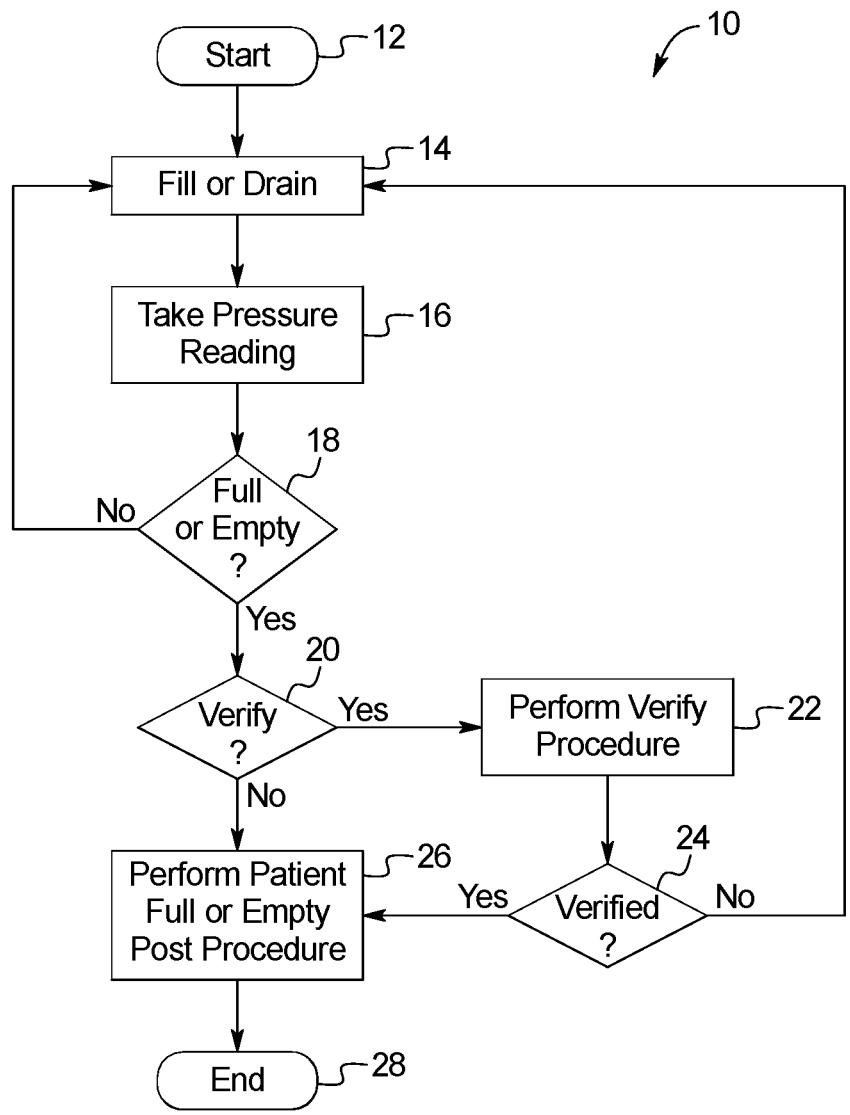
FIG. 1 is a process flow diagram illustrating various embodiments for the patient pressure pumping methodology of the present disclosure.

Referring now to the drawings and in particular to FIG. 1, various embodiments for the patient pressure pumping methodology of the present disclosure are illustrated by method 10. At oval 12, method 10 begins. At block 14, method 10 performs a portion of a fill or drain procedure. In one embodiment, the fill or drain procedure is a peritoneal dialysis ("PD") procedure that is performed as part of a PD cycle, wherein there may be multiple fill, dwell and drain cycles over the course of a PD treatment. It should be appreciated however that the fill or drain procedure of block 14 is applicable to any type of medical fluid delivery in which a medical fluid is delivered to (and possibly removed from) and collected in an area of the patient's body where pressure may build. Besides PD, the present systems and methods are also applicable to medical or nutritional fluid delivery.

Block 16 and diamond 18 form a sequence in which it is determined whether the patient is completely full during a fill procedure or completely empty during a drain procedure. At block 16, method 10 takes at least one pressure reading indicative of a pressure of medical fluid residing inside of the patient. If the medical fluid delivery is a PD delivery, the pressure inside of the patient is that of the patient's peritoneal cavity or intraperitoneal pressure ("IPP"). But as mentioned above, the patient pressure may be elsewhere in the patient's body, such as the patient's stomach or other cavities.

Figures 2, 3:
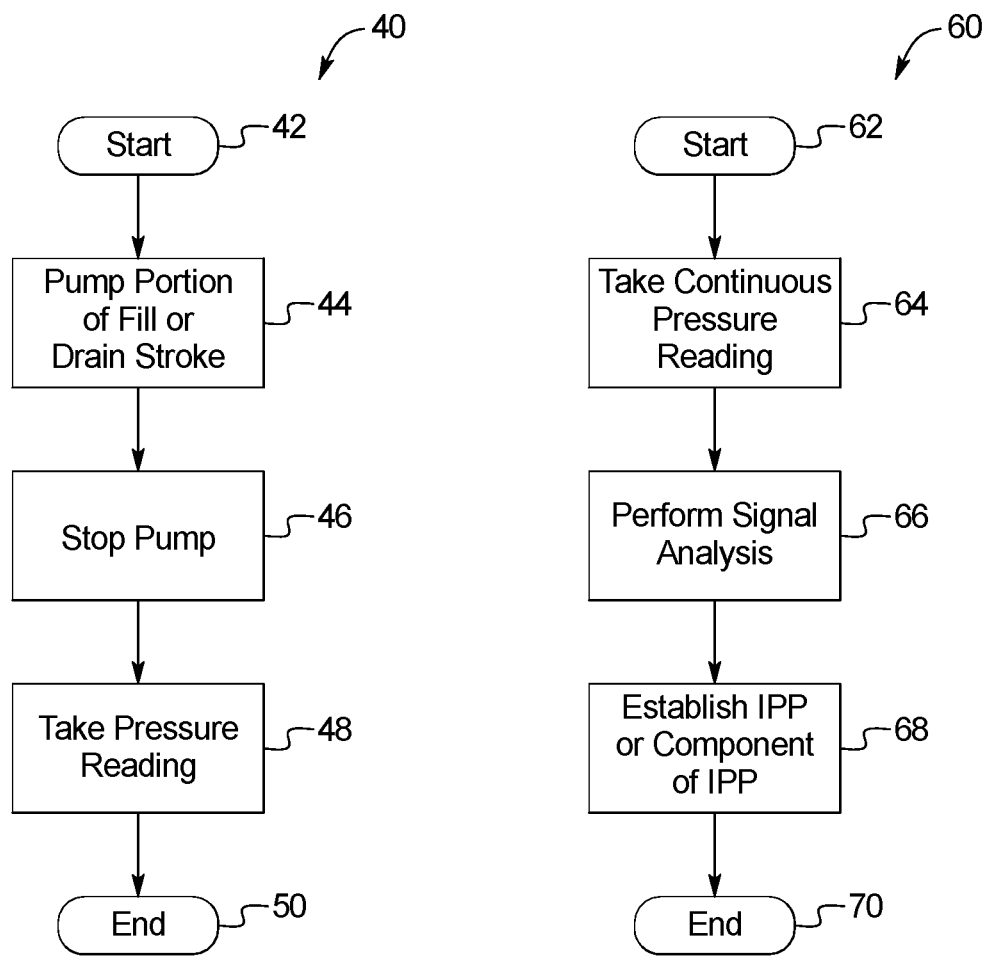
FIG. 2 is a process flow diagram illustrating one embodiment for taking a patient pressure reading used in the methodology of FIG. 1.
FIG. 3 is a process flow diagram illustrating another embodiment for taking a patient pressure reading used in the methodology of FIG. 1.

There are two primary embodiments for taking the at least one pressure reading at block 16. FIG. 2 illustrates one primary pressure reading embodiment in which pumping is paused to allow the pumping pressure to subside so that the pressure measured is that of the patient instead of the pump. The methodology of FIG. 2 may take different forms depending upon the type of medical fluid delivery pump used as discussed below. FIG. 3 illustrates another primary pressure reading embodiment in which pressure readings are taken continuously or semi-continuously (e.g., at a processor clock cycle) during pumping. The readings therefore show pressure waves that represent pressure due to the pump. Signal processing may be performed, however, which looks for a separate signal or component of the overall signal that represents or can be correlated to patient pressure, such as IPP. That signal or component signal is then used for the analysis of diamond 18.

At diamond 18, it is determined whether the pressure reading(s) indicate the patient is full (for a patient fill) or empty (for a patient drain). There are a number of different embodiments for performing the analysis of diamond 18. In one embodiment, the one or more pressure reading is compared to one or more prior reading to look for a pressure difference or slope of a pressure curve that indicates that a pressure spike is beginning or underway. As illustrated below in connection with FIG. 4, when a PD patient begins to become full, the peritoneal cavity tends to resist the introduction of additional dialysis fluid, causing the pressure inside the cavity to increase faster than previously (where previous pressure increase is due to an increase in head height of medical fluid accumulating inside the peritoneal cavity). In this embodiment, the pressure difference is assessed to determine if the patient is full (or near full). Looking at a pressure difference, as opposed to a pressure reading compared to a pressure limit may be advantageous because determining a pressure limit that is accurate for multiple patients may be difficult, and further, determining a pressure limit for a single patient that is accurate over multiple treatments may also be difficult. Patient pressure in the same treatment may vary, for example, due to relative head height changes between the patient and the machine.

The assessment may be performed in a variety of ways. In one implementation, the current pressure reading (or current average of multiple pressure readings) is compared to a previous pressure reading (or previous average of multiple pressure readings) to create a current pressure difference, which is compared with a pressure difference limit. In another implementation, the current pressure difference is averaged with at least one previous pressure difference and compared to a pressure difference limit. In a further alternative implementation, the current pressure difference is compared with one or more previous pressure differences to determine if a change in the slope indicates that the patient is full. For example, the control unit of the machine may look for a new slope that is at least twice as much as the old slope to determine if the patient is full.

The algorithm programmed into the control unit of the medical fluid delivery machine may employ a smoothing filter to smooth the patient pressure (e.g., IPP) data versus patient medical fluid volume data to help detect a point of significant slope increase (e.g., two times or more). The smoothing algorithm may involve the use of an approximating function that captures patterns in the data while filtering out noise.

Regardless of which implementation of the pressure difference or pressure spike embodiment is used for the determination at diamond 18, if the determination passes whatever criterion is used, the patient is determined not to be full (or near full) and method 10 returns to block 14 to continue the patient fill. The loop between patient fill at block 14, pressure reading at block 16 and the patient full (or near full) or not full determination at diamond 18 is repeated until the pressure difference determination fails to meet the criterion, at which point method 10 moves on to determine whether there is a verification determination at diamond 20.

In another embodiment for the determination at diamond 18, the one or more pressure reading is compared to a pressure limit, wherein the pressure limit indicates that the patient is full or close to being full. In a patient fill procedure, for example, the pressure reading may be compared to a pressure limit (e.g., standard pressure limit or pressure limit determined for the particular patient or a particular type of patient (e.g., height, weight, type of transporter, and/or sex) at a particular relative head height with the medical fluid delivery machine. If the pressure reading is at or below the limit in diamond 18, the patient is determined not to be full (or near full) and method 10 returns to block 14 to continue the patient fill. The loop between patient fill at block 14, pressure reading at block 16 and the patient full (or near full) or not full determination at diamond 18 is repeated until the pressure reading meets or exceeds the pressure limit, at which point method 10 moves on to determine whether there is a verification determination at diamond 20.

In a further alternative embodiment for the determination at diamond 18, a combination of the first and second embodiments may be employed. For example, any of the pressure difference implementations may be combined with a pressure limit, which may look to the pressure difference analysis unless the currently measured one or more readings is outside of the limit, in which case the patient is determined to be full (or near full). For example, a doctor or clinician may prescribe a maximum safe pressure for the patient, which will not be surpassed regardless of what the pressure difference information is providing. In this further alternative embodiment, again, the loop between patient fill at block 14, pressure reading at block 16 and the patient full (or near full) or not full determination at diamond 18 is repeated until either the pressure difference determination fails to meet the criterion or the pressure limit is met or exceeded, at which point method 10 moves on to determine whether there is a verification determination at diamond 20.

Verification determination at diamond 20 is meant in one embodiment to show that there may not be any verification at all and that the determination at diamond 18 is enough to adequately determine whether the patient is full (or near full) of medical fluid or not. Verification determination at diamond 20 is meant in another embodiment to show that verification is contingent and may not always be performed. Verification when performed may be performed in different ways. For example, if at diamond 18 the pressure reading is compared to a pressure limit, verification at block 22 may involve taking one or more additional pressure reading to determine if the reading is consistently (e.g., on average) at or above the pressure limit. The additional one or more pressure reading at verification determination 20 may or may not involve first pumping a small amount of additional treatment fluid to the patient.

Figure 5:
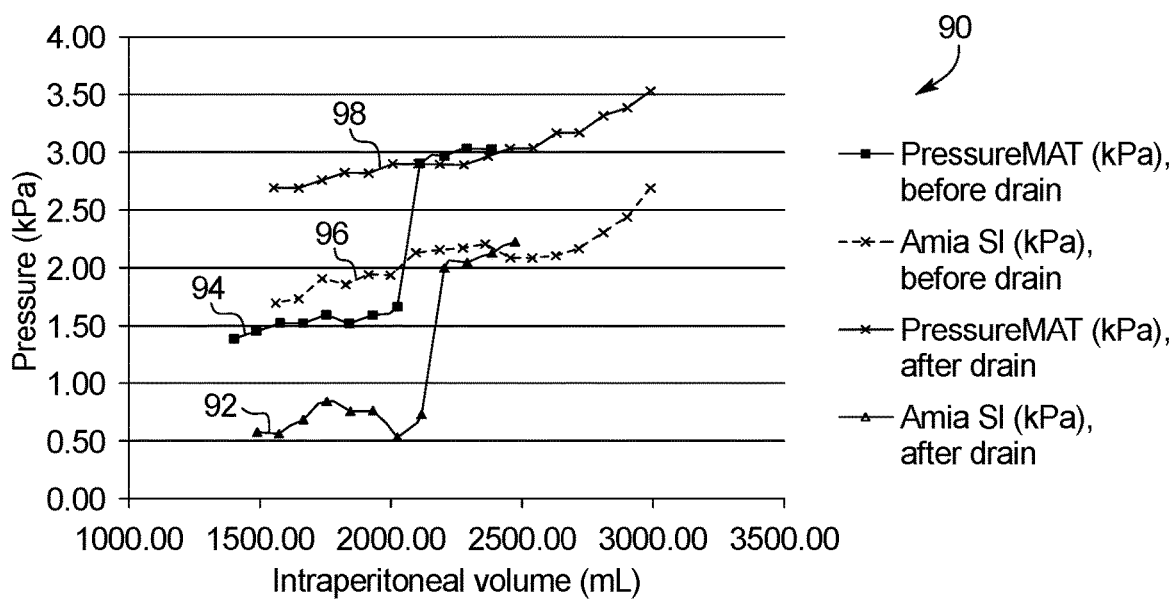
FIG. 5 is a plot illustrating the output of one embodiment of a verification routine of the pressure disclosure.

Alternatively, an amount of fluid may first be removed from the patient, followed by a pressure measurement, after which the same amount is pumped back to the patient and a second pressure measurement and evaluation is performed according to one of the embodiments for diamond 18. FIG. 5 illustrates example results of this procedure. By subtracting and adding back an amount of fluid (e.g., around 112 ml), the control unit of the machine can determine if the pressure spike or limit break is due to the patient being full (spike seen gain) or to another factor (e.g., change in head height, coughing, or line occlusion), where the spike is not seen again. The fluid removal, pressure reading, fluid added back, pressure reading and subsequent diamond 18 evaluation may be repeated one or more time to come to a final conclusion.

As indicated at diamond 24, for any of the above verification embodiments, if the verification results are not consistent with the patient being full (or near full), then method 10 returns to fill or drain at block 14, starting the entire procedure just described over again. Inconsistent results at diamond 24 may be due to a system noise factor, such as patient movement, coughing, or changing head height (see, e.g., FIG. 5 for effects of change of patient head height). Alternatively, (i) if the verification results are consistent with the patient being full (or near full) or (ii) there is no verification as determined at diamond 20, then method 10 performs a patient fill (or empty) procedure as indicated by block 26.

The verification routines taught in connection with block 22 may performed contingent upon a finding that the patient full (or near full) determination at diamond 18 occurs at an unexpectedly low fill volume. As discussed before, the medical fluid delivery machine, such as an APD machine, knows how much medical fluid has been delivered to the patient, but does not know how much fluid actually resides inside of the patient due to the uncertainty involved with a residual patient volume prior to the patient fill. So an unexpectedly low fill volume could mean that the patient had a large residual volume prior to the fill, and that the patient full (or near full) determination is correct, however, the associated unexpectedly low fill volume increases the likelihood of system noise leading to the patient full (or near full) determination. Here then, the selected verification routine of block 22 is performed. But if the patient full (or near full) determination at diamond 18 is accompanied by a fill volume consistent with the patient being full, no verification routine is performed.

At block 26, method 10 has determined that the patient is completely full (or near full). At block 26, method 10 performs a corresponding procedure, which may be one of multiple embodiments. In one embodiment, if the fill volume delivered at the patient pressure leading to the conclusion that the patient is full (or almost full) is consistent with an expected complete fill volume, then the determined fill volume, e.g., for APD, is set as the prescribed fill volume for subsequent cycles. Here, patient pressure measurements are not taken in the subsequent cycles in one implementation. Alternatively, even though the fill volume is set in the subsequent cycles, patient pressure is taken (e.g., according to FIG. 2 or FIG. 3) at or near the time that the prescribed fill volume is being reached inside the patient to see how consistent the full (or near full) patient pressure measurement maps against the prescribed fill volume, which may be accumulated in a file particular to the patient, which is useful for later evaluation.

If the fill volume delivered at the verified patient pressure leading to the conclusion that the patient is full (or almost full) is not consistent with an expected complete fill volume, e.g., the patient had significant residual volume before the fill, then the determined fill volume in method 10, e.g., for APD, is not set as the prescribed fill volume for subsequent cycles. Instead, method 10 up to the verification determination at diamond 24 just described is repeated in the next cycle, and in additional cycles if needed, until a fill volume corresponding to a patient pressure leading to the conclusion that the patient is full (or almost full) is consistent with an expected complete fill volume, upon which that fill volume is set as the prescribed fill volume for the remaining cycles.

In an alternative embodiment for block 26 of method 10, method 10 up to the verification determination at diamond 24 just described is repeated for each subsequent cycle of a treatment. For each cycle, fill volume delivered and the verified patient pressure leading to the conclusion that the patient is full (or almost full) is recorded in a file particular to the patient, which is useful for later evaluation. For each of the embodiments described for block 26 it is contemplated in an embodiment to not allow a fill volume to exceed a fill volume limit prescribed by a doctor or clinician even if the patient pressure measurements indicate that the patient is not yet full. It is contemplated, however, to record the patient pressures when the fill volume limit is reached, so that if the patient pressures consistently show that the patient may be able to receive larger fill volumes, the patient's machine operating prescription can be so modified.

At oval 28, method 10 ends. Method 10 has been described primarily in connection with a patient fill. As illustrated at block 14, and as mentioned briefly above, method 10 is not limited to a patient fill procedure and additionally includes patient drain procedures. Patient drain procedures involve the application of negative pressure to the patient. It should also be appreciated that the above method at virtually each step includes alternative embodiments, and in some cases alternative implementations of a same embodiment. To list each distinct combination setting forth each possibility is not necessary, and it should instead be appreciated that each possible combination of alternatives, except where expressly disclaimed, is contemplated.

Referring now to FIG. 2, various embodiments for taking the one or more pressure reading at block 16 of method 10 of FIG. 1 are illustrated by method 40. At oval 42, method 40 begins. At block 44, a medical fluid pump pumps an amount of medical fluid to or from the patient. At block 46, pumping is stopped for a period of time to allow pressure of the fluid (i) in the pump, (ii) in a line leading from the pump to the patient, and (iii) inside the patient to not reflect the pumping pressure and instead reflect the pressure of fluid inside the patient, which until the patient becomes full is the head height of fluid in the patient. At block 48, one or more pressure reading of the medical fluid is taken, which represents the current patient fluid pressure, i.e., IPP for PD. If multiple pressure readings are taken at block 48, they may be averaged to provide an averaged patient pressure for the current pressure reading session at block 48, which is recorded by a control unit of a medical fluid delivery device pumping the medical fluid. Again, the recorded pressure may be positive for a patient fill or negative for a patient drain. At oval 50, method 40 ends.

The amount of medical fluid pumped at block 44 is chosen to balance the sensitivity of the overall system and method with the desire not to interrupt filling or draining too often, thereby impeding treatment. That is, it is desired in one sense to make the amount of medical fluid pumped at block 44 small, so that more data points are produced and the system is able to react quicker to the patient becoming completely full (or near full) or completely empty (or near empty). On the other hand, it is desirable not to interrupt treatment too often, delaying overall treatment time and/or affecting dose rate. In an APD example, in which typical fill volumes may be about 2000 to 2500 mL's, a prudent amount of medical fluid pumped at block 44 before stopping for a pressure measurement at block 46 may be from about 45 mL's to about 90 mL's. If a volumetric or membrane pump is used, a full stroke volume may be from about 16 mL's to 25 mL's. In the example, and depending on the stroke volume and the amount pumped at block 44, a pressure reading at block 46 may then be taken once every two to five pump-out strokes. In an example, the amount of time needed at block 46 to take a proper pressure measurement indicative of a pressure inside the patient is from about three seconds to about thirty seconds.

Referring now to FIG. 3, various alternative embodiments for taking the one or more pressure reading at block 16 of method 10 of FIG. 1 are illustrated by method 60. The primary difference between method 40 of FIG. 2 and method 60 of FIG. 3 is that method 40 stops pumping and waits for the pressure measurement to reflect the pressure of the patient, while method 60 takes pressure measurements during pumping and attempts to pull out a component of the pressure reading indicative of patient pressure from the remaining components of the pressure reading.

At oval 62, method 60 begins. At block 64, method 60 causes a pressure sensor to take a continuous or semi-continuous (e.g., once every processing cycle) reading during a patient pump fill or pump drain operation. The pressure sensor may be mounted in any area of a fluid handling device, e.g., a disposable cassette or associated fluid lines for PD, an infusion pump set for medical or nutritional fluid delivery, and the like, which contacts the medical fluid delivered or removed. The pumping may be via a volumetric or membrane type pump, via a peristaltic type pump, or a syringe pump.

At block 66, method 60 performs a signal analysis on the received pressure signal. The signal analysis may, for example, involve a Fast Fourier Transform ("FFT") that converts a time dependent signal into a frequency domain (and vice versa), wherein different frequencies may be analyzed individually. Suitable FFT algorithms for performing the FFT include, but are not limited to, the Cooley-Tukey algorithm, Bluestein's FFT algorithm, Bruun's FFT algorithm, the Hexagonal Fast Fourier Transform, the Prime-factor FFT algorithm, and Rader's FFT algorithm.

At block 68, method 60 looks at the processed pressure signal or a component of the processed pressure signal that represents or may be correlated to the patient's internal pressure, e.g., IPP for PD. For example, experimentation may show that a particular frequency of a FFT represents or may be correlated to the patient's internal pressure. The control unit of the medical fluid delivery machine is programmed to analyze this particular frequency as the pressure readings are taken. The analysis may include any type of frequency filtering, including but not limited to the use of low-pass filters, high-pass filters, Twin T Active Notch filters, bandpass filters, and combinations thereof, along with any suitable and desired frequency amplification. The control unit may also convert the frequency analyzed into a value that represents the patient's internal pressure. The value is then analyzed according to any of the embodiments discussed above in connection with the full or empty diamond 18 of method 10. At oval 70, method 60 ends.

Figure 4:
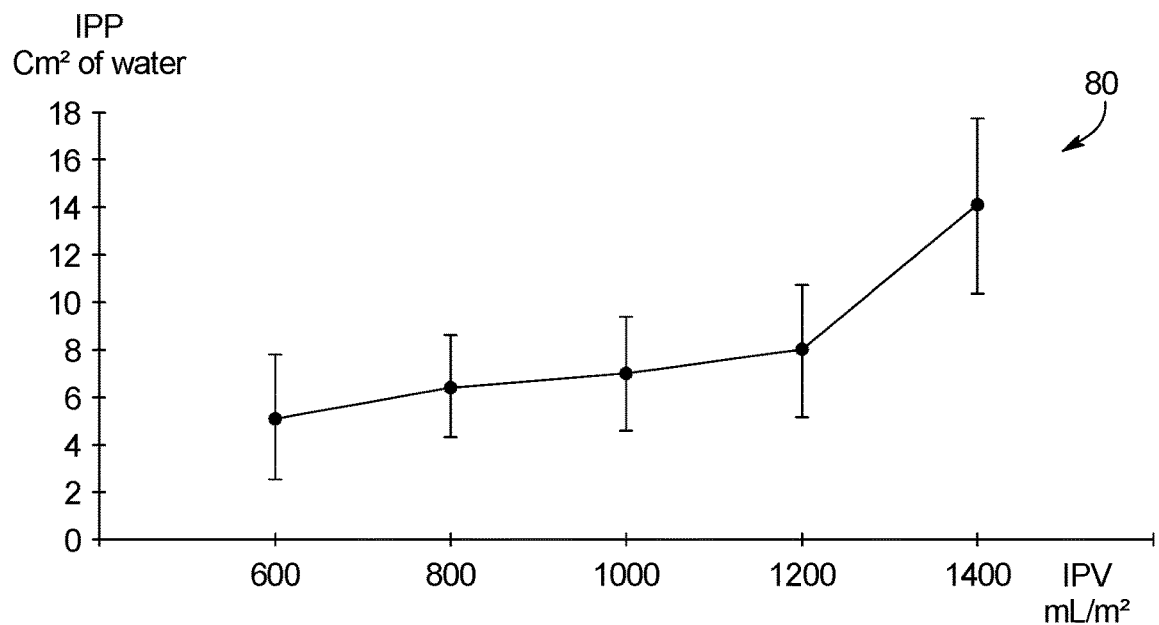
FIG. 4 is a plot illustrating how patient pressure varies relative to how full a cavity inside the patient is with a medical fluid.

Referring now to FIG. 4, a plot 80 showing how patient pressure varies relative to how full a cavity inside the patient is with a medical fluid. Plot 80 in particular illustrates a filling of patient's peritoneal cavity. Plot 80 shows IPP on the vertical axis measured in centimeters ("cm's") of water versus a volume of fluid in the patient's peritoneal cavity measured in milliliters per meters squared ("mL/m²"). As shown, IPP increases linearly assuming a constant fill rate due to the head height of liquid in the patient's peritoneum increasing. At about 1200 mm³ of fluid volume, the patient's peritoneum begins to become full and the change in pressure for the same increment in fluid volume increases. The increase in slope may be two times or more. The increase is due to the fluid pushing against the peritoneal wall and the corresponding reactive force by the peritoneal wall on the fluid.

It is accordingly contemplated in an embodiment to look for (and possibly verify) the change in slope to determine that the patient is full (or near fill) and to take appropriate action, e.g., stop the peritoneal cavity fill and begin a dwell portion of the cycle. In an embodiment, the fill is stopped within the 200 mm³ fill volume window illustrated in plot 80 of FIG. 4 between 1200 mm³ and 1400 mm³.

Referring now to FIG. 5, a graph 90 showing the output of an example verification routine is illustrated. Graph 90 shows IPP on the vertical axis measured in kPa versus volume of fluid in the patient's peritoneal cavity measured in mL's. Graph 90 is actually four plots 92, 94, 96 and 98. Plots 92 an 94 show a step change in slope at about 2000 mL of dialysis fluid volume in the patient's peritoneum. These step changes could be due to the patient's peritoneal cavity being full or due to an outside noise factor, such as patient movement, coughing or the changing of patient head height relative to the machine.

A verification routine, such as any described above in connection with diamond 20 of method 10, may therefore be performed to see if the step change in slope indicates the patient being full. In one example an amount, e.g., about 100 to about 600 mL, is removed from the patient and then returned to the patient to see if the step change in slope still exists, indicating that the patient is full. In graph 90, plot 96 corresponds to plot 92 after its verification routine, while plot 98 corresponds to plot 94 after its verification routine. In both plots 96 and 98, the volume is reduced from the spike volume. That is, the volume at the spike of about 2100 to 2200 mL in plot 92 is reduced to about 1500 mL at the beginning of plot 96. The volume at the spike of about 2000 to 2100 mL in plot 94 is reduced to about 1500 mL at the beginning of plot 98. In both plots 96 and 98, the slope returns to substantially the same slope prior to the step slope changes in plots 92 and 94, respectively, indicating that the patient is not yet full and that the step slope change is due to another factor, here, likely head height change since IPP in the after routine plots 96 and 98 remains at the increased pressure amounts.

Figure 6:
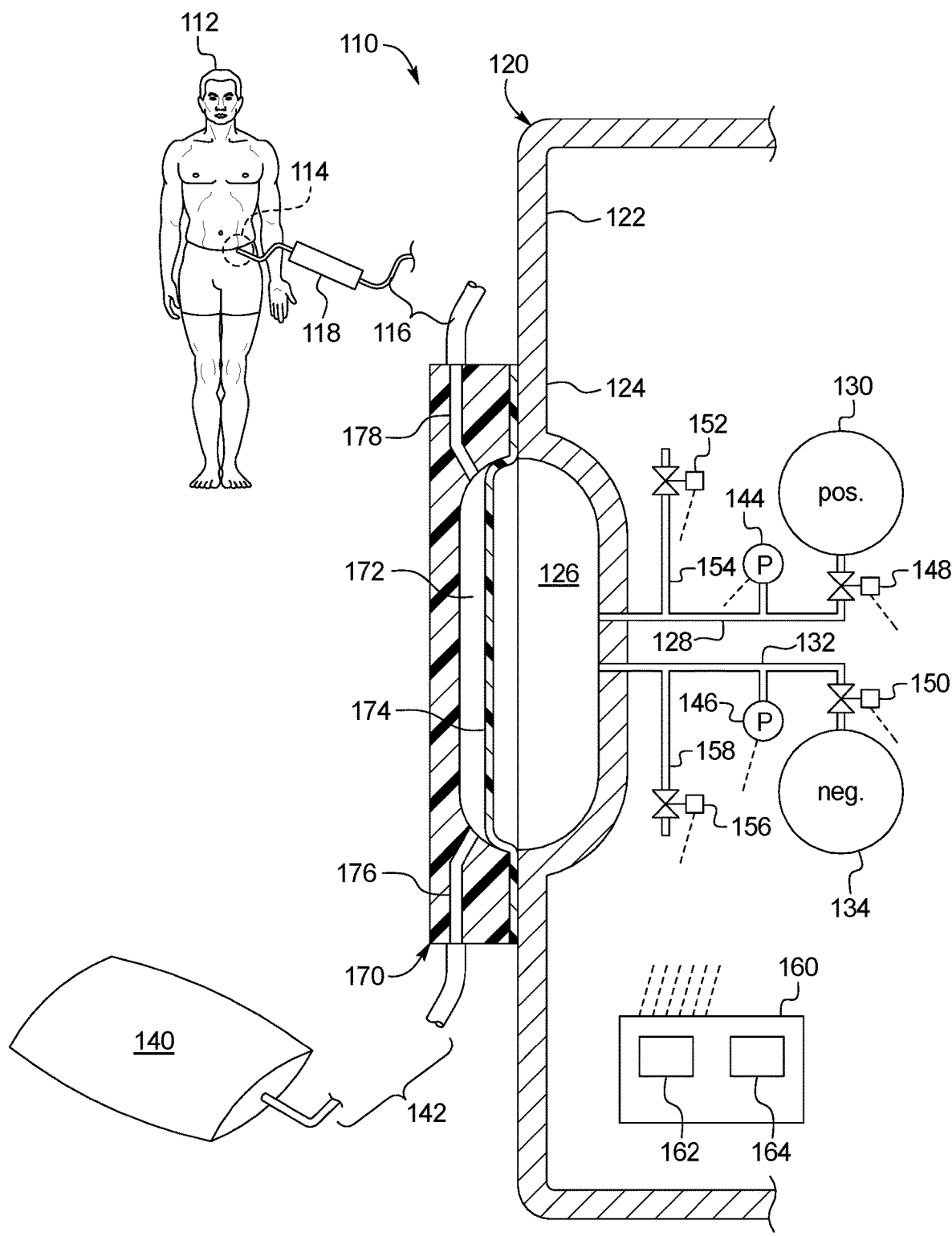
FIG. 6 is a schematic view illustrating one example apparatus for implementing the patient pressure pumping methodology of the present disclosure.

Referring now to FIG. 6, an example system 110 for operating subroutine 40 of FIG. 2 is illustrated. System 110 includes a machine 120, such as an APD machine, operating a medical fluid handling device 170, such as a dialysis fluid cassette. Machine 120 includes a housing 122 defining a pump interface 124 having a pump actuator or pump actuation area 126 for actuating medical fluid handling device 170. Pump actuation area 126 in the illustrated embodiment is actuated pneumatically via a positive pneumatic line 128 extending from a positive pneumatic source 130 to perform a pump-out stroke, e.g., to push (i) fresh dialysis fluid to a peritoneal cavity 114 of patient 112 via a patient line 116 and patient transfer set 118 or (ii) used dialysis fluid to a drain. Pump actuation area 126 in the illustrated embodiment is actuated pneumatically via a negative pneumatic line 132 extending from a negative pneumatic source 134 to perform a pump-in stroke, e.g., to pull fresh dialysis fluid from a dialysis fluid source 140 through a supply line 142 or used dialysis fluid from peritoneal cavity 114 of patient 112 via patient line 116 and transfer set 118.

Machine 120 also provides a pressure sensor 144 for measuring positive pressure in positive pneumatic line 128 and a pressure sensor 146 for measuring negative pressure in negative pneumatic line 132. Machine 120 further includes plural electrically operated pneumatic valves, e.g., valves 148, 150, 152 and 154. Pneumatic valve 148 is positioned in positive pneumatic line 128 to selectively allow positive pressure from source 130 to reach pump actuation area 126. Pneumatic valve 150 is positioned in negative pneumatic line 132 to selectively allow negative pressure from source 134 to reach pump actuation area 126. A vent valve 152 is provided in a vent line 154 in communication with positive pneumatic line 128 to selectively vent positive pressure in line 128 and pump actuation area 126 to atmosphere. A second vent valve 156 is provided in a vent line 158 in communication with negative pneumatic line 132 to selectively vent negative pressure in line 132 and pump actuation area 126 to atmosphere. In an alternative embodiment, a single vent valve and line may be provided to vent both positive and negative pressure from pump actuation area 126 to atmosphere.

Pressure sensors 144 and 146 and pneumatic valves 148, 150, 152 and 154 are each illustrated with extending dashed electrical and/or signal lines. Machine 120 is also provided with a control unit 160 having one or more processor 162 and one or more memory 164. Control unit 160 may have any one or more of a master controller, safety controller, video controller, and/or sub- or delegate controller. Control unit 160 is also illustrated with extending dashed electrical or signal lines that extend to the pressure sensors and pneumatic solenoid valves. Control unit 160 receives pressure readings from pressure sensors 144 and 146 and selectively opens and closes pneumatic solenoid valves 148, 150, 152 and 154. It should be appreciated that control unit 160 may operate with additional pressure sensors, valves, fluid heater, which are not illustrated to simplify FIG. 6.

Medical fluid handling device 170 is provided with a pump actuation chamber 172 that mates with pump actuation area 126 to form an overall pumping chamber. Medical fluid handling device 170 in the illustrated embodiment includes a flexible membrane, diaphragm or sheet 174, which may be sized to fit pump actuation chamber 172 or be sized to cover a whole side of medical fluid handling device 170 (as illustrated), wherein a portion of the membrane 174 covers pump actuation chamber 172, and wherein such portion may be at least substantially flat or be pre-domed or pre-shaped to fit into one or both pump actuation area 126 and pump actuation chamber 172. Membrane 174 (or separate membranes) may also cover and be used to actuate medical fluid valves (not illustrated), such as (i) a fluid valve positioned and arranged to selectively allow medical fluid to flow from fluid source 140, through supply line 142 and a supply channel 176 of medical fluid handling device 170 to pump actuation chamber 172 and (ii) a fluid valve positioned and arranged to selectively allow medical fluid to flow from pump actuation chamber 172 through a patient channel 178 of medical fluid handling device 170, through patient line 116 and patient transfer set 118 to peritoneal cavity 114 of patient 112. It should be appreciated that medical fluid handling device 170 may have additional fluid valves, e.g., additional fluid valves for an additional pump actuation chamber 172 (alternating to provide more continuous flow) and additional fluid valves for multiple supply lines 142, a fluid heater line, and/or a drain line, which are not illustrated to simplify FIG. 6.

Control unit 160 causes negative pressure from source 134 to be applied to flexible membrane 174 to pull the sheet against the wall of pump actuation area 126 to correspondingly pull medical fluid into pump actuation chamber 172. To do so, control unit causes valves 148, 152 and 156 to be closed and valve 150 to be open. During the fill of pump actuation chamber 172, pressure sensor 146 measures negative pumping pressure.

Control unit 160 causes positive pressure from source 130 to be applied to flexible membrane 174 to push the sheet against the wall of pump actuation chamber 172 to correspondingly push medical fluid from pump actuation chamber 172. To do so, control unit causes valves 150, 152 and 156 to be closed and valve 148 to be open. During the discharge of pump actuation chamber 172, pressure sensor 144 measures positive pumping pressure.

To take a patient pressure reading according to subroutine 40 of FIG. 2 during pump actuation chamber 172 (filling the patient), control unit 160 in one embodiment closes positive pressure pneumatic valve 148 mid-stroke so that flexible membrane 174 is only partially moved towards the wall of pump actuation chamber 172, as is illustrated in FIG. 6. Control unit 160 causes vent valve 152 to open, enabling the positive pressure in pump actuation area 126 and positive pneumatic line 128 to vent to atmosphere. Once the positive pneumatic pressure is vented, control unit closes vent valve 152. The pressure that pressure sensor 144 now reads is the positive IPP within peritoneal cavity 114 of patient 112. Multiple such readings may be taken and averaged at control unit 160.

To take a patient pressure reading according to subroutine 40 of FIG. 2 during pump actuation chamber 172 fill (emptying the patient), control unit in one embodiment 160 closes negative pressure pneumatic valve 150 mid-stroke so that flexible membrane 174 is only partially moved towards the wall of pump actuation area 126, as is illustrated in FIG. 6. Control unit 160 causes vent valve 156 to open, enabling the negative pressure in pump actuation area 126 and negative pneumatic line 132 to vent to atmosphere. Once the negative pneumatic pressure is vented, control unit closes vent valve 156. The pressure that pressure sensor 146 now reads is the negative IPP within peritoneal cavity 114 of patient 112. Multiple such readings may be taken and averaged at control unit 160.

As discussed above, control unit 160 in one embodiment repeats the pressure measurement sequence (positive or negative) periodically during a patient fill (or drain), e.g., once every 100 to 150 mL's of dialysis fluid fill volume, wherein a full pump stroke may be about 20 mL's. The pump pausing and pressure measurement sequence may take, e.g., three to thirty seconds to complete.

The system and method of the present disclosure are not limited to pneumatic pumping or to the membrane or volumetric type of pumping illustrated and described in connection with FIG. 6. Alternatively, for example, machine 120 may instead provide a peristaltic pump actuator that operates with a section of tubing provided by an alternative medical fluid handling device 170. The tubing downstream from the peristaltic pump actuator (between the actuator and patient 112) may be provided with a pressure sensing area (e.g., a puck type structure with a flexible sensing membrane) that is sensed by a pressure sensor located on or within housing 122 of machine 120 so as to contact the pressure sensing area of the tube. Control unit 160 may be programmed to pause the peristaltic pump actuator at desired intervals to allow the pumping pressure to subside, and for the pressure sensor to instead read positive or negative patient pressure, such as IPP.

The alternative structure just described may also be used to perform subroutine 60 of FIG. 3. Here, instead of pausing the peristaltic pump actuator, control unit 160 takes a continuous reading, or readings at every clock cycle of processor 162, and performs the signal analysis of block 66 and the patient pressure establishment of block 68 described above in subroutine 60 of FIG. 3.

Figure 7:
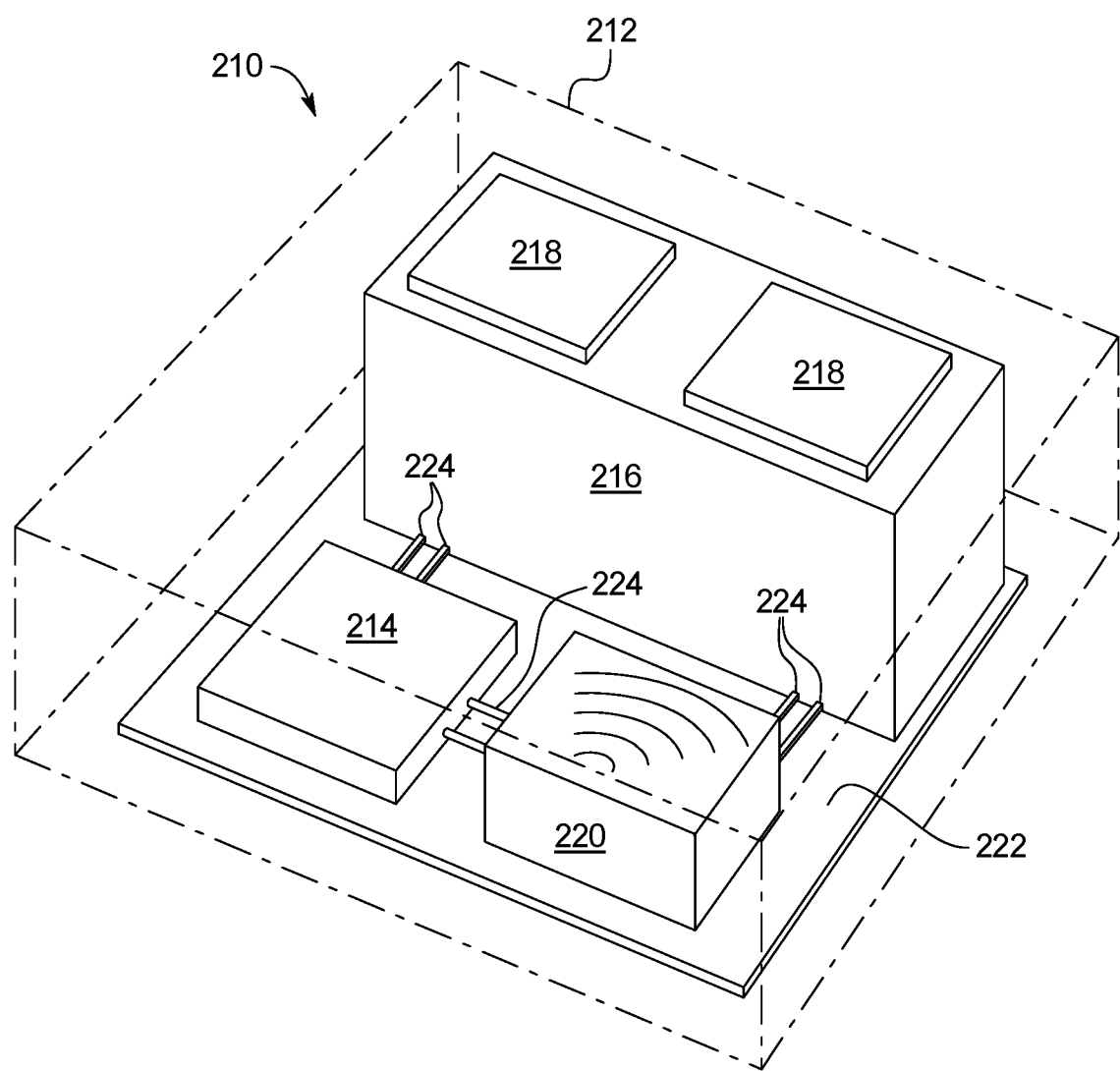
FIG. 7 is a schematic view illustrating another example apparatus for implementing the patient pressure pumping methodology of the present disclosure.

Referring now to FIG. 7, a micromechanical ("MEMS") apparatus 210 is illustrated. MEMS apparatus 210 in the illustrated embodiment includes a housing 212 holding three primary components including a power supply 214, a MEMS sensor 216 and a wireless transmitter 220, which are each soldered to a small printed circuit board ("PCB") 222 located within housing 212 and connected to each other via traces 224 along PCB 222. Power supply 214 supplies power to MEMS sensor 216 and wireless transmitter 220. Power supply 214 may for example be a 5 VDC power supply and may only be required to supply power over the course of a single treatment.

Housing 212 as illustrated sealingly exposes the pressure sensing portions 218 of MEMS sensor 216, so that portions 218 may contact a medical fluid directly. Pressure signals from MEMS sensor 216 are sent via wireless transmitter 220 to a wireless receiver located within machine 120 and being either part of or in communication with control unit 160.

Viewing FIG. 6 additionally, it is contemplated to connect the bottom surface of housing 212 via adhesion, heat sealing, sonic welding or molding to or into an inside surface of any one or more of patient channel 178 of medical fluid handling device 170, patient line 116 connected to medical fluid handling device 170, or patient transfer set 118. In any of these locations, sensing portions 218 contact flowing medical fluid, enabling control unit 160 to take a continuous reading, or readings at every clock cycle of processor 162, via MEMS sensor 216, and perform the signal analysis of block 66 and the patient pressure establishment of block 68 described above in subroutine 60 of FIG. 3.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A medical fluid delivery machine operating a medical fluid handling device, the medical fluid delivery machine comprising:
   a pump interface including an actuation area for delivering positive pressure or negative pressure to the medical fluid handling device to move medical fluid into or out of the device, respectively, the medical fluid handling device capable of being placed in fluid communication with a patient;
   a pressure sensor positioned and arranged to measure pressure within the actuation area;
   a valve positioned and arranged to selectively vent the actuation area to atmosphere; and
   a control unit in signal communication with the pressure sensor and control communication with the valve, the control unit programmed to perform a sequence during pumping, in which the control unit
   (i) causes an application of positive pressure or negative pressure to the actuation area to be stopped, causes the valve to switch to vent the actuation area to atmosphere, then causes the valve to switch to close the actuation area to atmosphere, and records at least one pressure signal reading taken via the pressure sensor, and
   (ii) determines whether the application of the positive pressure or negative pressure to the actuation area should be resumed based on the at least one pressure signal reading.

2. The medical fluid delivery machine of claim 1, wherein the control unit includes at least one of (i) at least one processor, (ii) at least one memory, or (iii) at least one delegate controller.

3. The medical fluid delivery machine of claim 1, wherein the valve is a first valve, and which includes a second valve under control of the control unit, the control unit further programmed so that in (i), stopping the positive pressure or negative pressure to the actuation area includes switching the second valve to close the actuation area from a source of the positive pressure or negative pressure and in (ii), resuming application of the positive pressure or negative pressure to the actuation area includes switching the second valve to open the actuation area to the source of the positive pressure or negative pressure.

4. The medical fluid delivery machine of claim 3, wherein the pressure sensor is placed in fluid communication with a line leading from the source of the positive pressure or negative pressure to the actuation area.

5. The medical fluid delivery machine of claim 1, wherein the pumping includes a pump stroke having a pump stroke beginning and a pump stroke end.

6. The medical fluid delivery machine of claim 1, wherein the actuation area is a first actuation area and wherein the pump interface includes a second actuation area for delivering positive pressure or negative pressure to the medical fluid handling device to move medical fluid into or out of the device, and wherein the control unit is programmed to perform (i) and (ii) for both the first actuation area and the second actuation area.

7. The medical fluid delivery machine of claim 1, wherein determining if application of the positive pressure or negative pressure to the actuation area should be resumed includes the control unit being programmed to (iii) determine a pressure difference between the at least one pressure signal reading and at least one pressure signal reading from at least one previous sequence.

8. The medical fluid delivery machine of claim 7, wherein the control unit is programmed to (iv) resume pressure application if the pressure difference is at least substantially the same as a previously determined pressure difference.

9. The medical fluid delivery machine of claim 7, wherein the control unit is programmed to (iv) not resume pressure application if the pressure difference is different than a previously determined pressure difference.

10. The medical fluid delivery machine of claim 9, wherein a difference between the pressure difference and the previously determined pressure difference is required to be at least a certain amount not to resume pressure application.

11. The medical fluid delivery machine of claim 7, wherein the control unit is programmed (iv) such that if the pressure difference is different than a previously determined pressure difference, at least one additional sequence is performed and pressure application is not resumed if a new pressure difference is still different than the previously determined pressure difference.

12. The medical fluid delivery machine of claim 7, wherein the control unit is programmed (iv) such that if the pressure difference is different than a previously determined pressure difference, the control unit causes a reverse pumping of a medical fluid volume and then a re-reverse pumping of the medical fluid volume, and (v) performs (i) to (iii) again.

13. The medical fluid delivery machine of claim 12, wherein the control unit is programmed to not resume pressure application if the pressure difference in (iii) performed again is still different than the previously determined pressure difference.

14. The medical fluid delivery machine of claim 12, wherein the control unit is programmed to resume pressure application if the pressure difference in (iii) performed again is at least substantially the same as the previously determined pressure difference.

15. The medical fluid delivery machine of claim 12, wherein the sequence is for a patient fill in which positive pressure is applied in the actuation area, wherein the reverse pumping is a removal of the medical fluid volume from the patient and the re-reverse pumping is a return of the medical fluid volume to the patient, and wherein pressure within the actuation area is assumed to be pressure in the patient after the actuation area is vented to atmosphere and then closed to atmosphere.

16. The medical fluid delivery machine of claim 7, wherein the control unit is programmed to apply a smoothing filter to multiple pressure difference determinations in looking for a change in pressure differences indicating that pressure application should not be resumed.

17. The medical fluid delivery machine of claim 1, wherein determining if application of the positive pressure or negative pressure to the actuation area should be resumed includes determining if the at least one pressure signal reading is within a pressure limit.

18. The medical fluid delivery machine of claim 17, wherein the control unit is programmed not to resume pressure application if the at least one pressure signal reading is outside the pressure limit.

19. The medical fluid delivery machine of claim 1, wherein a time duration for (i) to be completed is about three to about thirty seconds.

20. The medical fluid delivery machine of claim 1, wherein the sequence is repeated during pumping in medical fluid volume increments.

21. A medical fluid delivery machine operating a medical fluid handling device, the medical fluid delivery machine comprising:
  a pump interface including an actuation area for delivering positive pressure to the medical fluid handling device to move medical fluid into or out of the device, respectively, the medical fluid handling device capable of being placed in fluid communication with a patient;
  a pressure sensor positioned and arranged to measure pressure within the actuation area;
  a valve positioned and arranged to selectively vent the actuation area to atmosphere; and
  a control unit in signal communication with the pressure sensor and control communication with the valve, the control unit programmed to perform a sequence during pumping, in which the control unit
    (i) causes an application of positive pressure to the actuation area to be stopped, causes the valve to switch to vent the actuation area to atmosphere, then causes the valve to switch to close the actuation area to atmosphere, and records at least one pressure signal reading taken via the pressure sensor, and
    (ii) determines whether the application of the positive pressure to the actuation area should be resumed based on the at least one pressure signal reading.

* * * * *